United States Patent
Brambilla et al.

(12)

(10) Patent No.: US 10,737,044 B2
(45) Date of Patent: Aug. 11, 2020

(54) AEROSOL INHALATION DEVICE

(71) Applicant: CHIESI FARMACEUTICI S.p.A., Parma (IT)

(72) Inventors: Gaetano Brambilla, Parma (IT); Robert Johnson, Parma (IT); David Andrew Lewis, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 775 days.

(21) Appl. No.: 15/276,291

(22) Filed: Sep. 26, 2016

(65) Prior Publication Data

US 2017/0080168 A1 Mar. 23, 2017

Related U.S. Application Data

(63) Continuation of application No. 14/012,392, filed on Aug. 28, 2013, now abandoned.

(30) Foreign Application Priority Data

Aug. 29, 2012 (EP) ..................................... 12182122

(51) Int. Cl.
*A61M 15/00* (2006.01)
*A61M 11/02* (2006.01)

(52) U.S. Cl.
CPC .......... *A61M 15/009* (2013.01); *A61M 11/02* (2013.01); *A61M 15/0021* (2014.02);
(Continued)

(58) Field of Classification Search
CPC ............ A61M 15/009; A61M 15/0021; A61M 15/0065; A61M 11/02
See application file for complete search history.

(56) References Cited

U.S. PATENT DOCUMENTS

| 3,361,306 A | 1/1968 | Grim |
| 5,435,297 A | 7/1995 | Klein |

(Continued)

FOREIGN PATENT DOCUMENTS

| EP | 0 132 352 | 1/1985 | |
| EP | 0132352 A2 * | 1/1985 | .......... A61M 15/009 |

(Continued)

OTHER PUBLICATIONS

International Search Report for PCT/EP2013/067514 dated Nov. 7, 2013.

(Continued)

*Primary Examiner* — Samchuan C Yao
*Assistant Examiner* — Margaret M Luarca
(74) *Attorney, Agent, or Firm* — Oblon, McClelland, Maier & Neustadt, L.L.P.

(57) ABSTRACT

Actuators for an aerosol inhalation device containing a housing adapted to receive an aerosol canister containing a pressurized medicament formulation, a mouthpiece portion through which the user inhales, a nozzle block and an orifice and a tubular element extending in the mouthpiece portion from the orifice aperture in a longitudinal axis substantially aligned with a longitudinal axis of the mouthpiece portion provide a significant reduction in the non-respirable, coarse fraction of the emitted aerosol medicament via inertial impaction and retention in the actuator than in the oropharynx, with consequent less associated side effects and oral candidiasis in the patient. In addition the presence of the tubular element has minimal, negligible impact on the fine particle dose and on the particle size distribution (PSD) of the delivered particles having aerodynamic diameter lower than 9 μm.

19 Claims, 11 Drawing Sheets

(52) U.S. Cl.
CPC . *A61M 15/0065* (2013.01); *A61M 2205/0233* (2013.01); *A61M 2205/0238* (2013.01); *A61M 2209/06* (2013.01)

(56) References Cited

U.S. PATENT DOCUMENTS

| | | | |
|---|---|---|---|
| 5,682,875 A * | 11/1997 | Blower | A61M 15/009 128/200.14 |
| 2003/0015191 A1 * | 1/2003 | Armstrong | A61M 15/0028 128/200.21 |
| 2005/0274378 A1 | 12/2005 | Bonney et al. | |
| 2006/0118107 A1 | 6/2006 | King | |
| 2007/0251950 A1 | 11/2007 | Bacon | |
| 2010/0218760 A1 | 9/2010 | Anderson | |
| 2011/0061646 A1 | 3/2011 | Crosby | |
| 2011/0155129 A1 | 6/2011 | Stedman et al. | |
| 2012/0085345 A1 | 4/2012 | Zeng et al. | |

FOREIGN PATENT DOCUMENTS

| | | |
|---|---|---|
| GB | 1 219 090 | 1/1971 |
| GB | 2 312 379 | 10/1997 |
| GB | 2 415 388 A | 12/2005 |
| WO | 94/27663 | 12/1994 |
| WO | 2008/017575 | 2/2008 |
| WO | 2011/095762 | 8/2011 |

OTHER PUBLICATIONS

International Preliminary Report on Patentability for PCT/EP2013/067514 dated Mar. 3, 2015.
European Search Report in Application No. 12182122.7, dated Jan. 22, 2013.

* cited by examiner

AEROSOL INHALATION DEVICE

CROSS REFERENCES TO RELATED APPLICATIONS

This application is a continuation of U.S. application Ser. No. 14/012,392, filed Aug. 28, 2013, and claims priority to European Patent Application No. 12182122.7 filed on Aug. 29, 2012, the entire contents of each of which is incorporated herein by reference in its entirety.

BACKGROUND OF THE INVENTION

Field of the Invention

The present invention relates to the field of inhalers for medicaments and in particular to an improvement of aerosol devices for transferring to the respiratory system of a patient and in particular to the lungs, by oral inhalation, a metered dose of a medicament contained in a pressurised dispensing container.

Discussion of the Background

The use of aerosol inhalation devices for the administration by inhalation of medicaments in form of aerosol is well known. Among the devices available to deliver medicaments to the lungs, pressurised metered-dose inhalers (pMDIs) are widely used.

pMDIs are aerosol delivery systems designed to deliver a medicament formulated with a pressure liquefied propellant gas and optionally at least one suitable additive. pMDIs are designed to meter a predetermined amount of the medicament, completely dissolved (in solution) or in form of micronized solid particles dispersed or suspended in the formulation and to dispense the dose as an inhalable aerosol cloud or plume.

A conventional pMDI is shown in FIG. 1. The pMDI comprises an actuator 1 comprising, in its vertical hollow portion, a housing adapted to receive a canister 2. The canister 2 contains a formulation wherein the medicament is in solution or in suspension with a low boiling point propellant system optionally comprising at least one suitable pharmaceutically acceptable additive. The canister 2 is normally provided with a metering valve having a hollow valve stem 3 for measuring discrete doses of the medicament formulation. The dose is dispensed as an inhalable cloud or plume 4.

Typical actuators 1 have a nozzle assembly or nozzle block 5 which receives the hollow valve stem 3 of the aerosol canister 2. The nozzle block 5 defines the walls of the valve stem receptacle 13, expansion chamber or sump 6, and orifice 7 which ends in an aperture 8 having an enlarging frusto-conical section terminating in a cylindrical parallel sided portion.

The orifice 7 through its aperture 8 serves to propel the aerosol formulation into the mouthpiece portion, towards a mouthpiece opening 10 and assists in atomization of the aerosol formulation. Traditionally, the orifice 7 has been provided such that its longitudinal axis is aligned with a longitudinal axis 9 of the actuator mouthpiece portion, so that the aerosol exits the orifice in a mean direction towards a mouthpiece opening 10. The longitudinal axis of the orifice 7 in the nozzle block 5, aligned with the longitudinal axis 9 of the mouthpiece portion, is normally located at an angle greater or equal to 90°, preferably in the range from approximately 90° to approximately 120°, and more preferably from approximately 90° to approximately 110° to the direction of the longitudinal axis of the hollow valve stem 3 of the aerosol canister 2. Therefore when the canister 2 is actuated, the formulation containing the propellant moves down the stem 3 and expands within the expansion chamber 6 before being propelled through the orifice 7 from its aperture 8 towards the mouthpiece opening 10. The formulation, therefore, is atomized in a direction extending at an angle from approximately 90° to approximately 120° and preferably 110° with respect to the longitudinal axis of the aerosol canister 2.

In known pMDIs the medicament is discharged in response to the user actuation performed by moving the canister relative to the valve stem, in the same time the medicament is inhaled by the user through the mouthpiece opening, creating an airflow entering from the spaces between the external walls of the canister and the internal walls of the vertical portion of the actuator, located upstream from the mouthpiece portion.

Typically in such devices, there is little or no restriction in the airflow between the entering air and the mouthpiece portion. Because of this, a substantial airflow may be created by a user of the device and, because the medicament is fired into the airflow in the same direction as the airflow, the effect is that emitted medicament particles can be travelling at quite substantial velocities, e.g. in excess of 40 m/s, when they reach the mouthpiece. As inhalers of this type are normally designed to be as small as practical for the convenience of users, the distance between the point at which the medicament is fired into the airflow and the patient's mouth is usually quite small so that there is little distance to reduce the inertia of the particles of medicament, with the result that coarse, non-respirable (>9 μm aerodynamic diameter) aerosol particles may impact and deposit in the mouth, throat and pharynx walls.

This is normally undesirable, since the medicaments were designed for delivery to the respiratory system and may not have an appropriate effect when deposited in the mouth and throat potentially causing oral candidiasis and dysphonia and systemic side effects, when allowed to enter the digestive tract by swallowing.

These effects can currently be prevented by the use of add-on devices, spacers or holding chambers such as the Volumatic™ and AeroChamber Plus™, which are able to prevent a large proportion of the coarse particles from the dose of the aerosol reaching the patient.

Various attempts have been made to modify the spray characteristics of inhalers. GB-A-2279879 and EP-A-0839544 disclose inhalers in which air inlets are arranged such that during inhalation an air flow is created which has a component directed away from the mouthpiece towards the aerosol spray. The reverse airflow component is intended to create turbulence and slow the velocity of the medicament particles.

EP-A-862921 discloses similar devices comprising also a flow controller manually depressible to unseal the air inlets.

WO 93/05837 and U.S. Pat. No. 4,972,830 disclose inhalers in which the passage which directs the pressurised medicament from the canister to the chamber has particular configurations to reduce the velocity of the spray and enhance dispersion of the medicament in the airflow.

EP-A-0412648 discloses an inhaler in which a frusto-conical diverter with a small orifice is positioned in the path of the spray before the mouthpiece. Aerosol droplets are said to predominantly pass through the small orifice, decelerate and be inhaled while the propellant gas is predominantly diverted away from the mouthpiece out of the inhaler.

WO 00/50112 relates to actuators arranged as to inhibit airflow due to patient in the vicinity of the orifice of the nozzle block.

An analogous principle has been followed in the three following applications directed to very similar devices:

WO 2008/023014 wherein the actuator outlet, through which the user inhales, has a substantially closed rear end section which partitions the outlet from the housing such that, on inhalation, an air flow is drawn substantially from an outer peripheral surface of the outlet;

WO 2008/023015 wherein the outlet includes at least one flow path which provides for a substantially annular air flow as to provide a sheathing air flow; and WO 2008/023018 wherein the nozzle outlet, coupled or integrally formed with the actuator outlet, is present as a separately-formed component from the nozzle block and may be provided with one or more air inlets of different shapes positioned around the orifice outlet of the nozzle block.

However, in these cases the drug delivery characteristics are not considered identical to a conventional pMDI product; and some of these devices are also bulky and inconvenient for the patients to carry with them, often leading to a reduction in patient compliance.

In WO 2012/032088, the actuator is designed such that atomized spray may be emitted from the orifice with a longitudinal axis which coincides with the longitudinal axis of the canister. However, the correct use of this actuator depends on the inspiratory effort and timing of the patient, moreover the manufacture of such a device is more complex and expensive than a conventional pMDI.

EP-A2-0132352, U.S. Pat. No. 3,361,306, and US-A1-2012/0085345 describe devices for dispensing medicaments from pressurised containers having an outlet spout provided internally with an outlet member having a small (capillary passage) arranged at one end to receive contents discharged from the pressurised container and terminating at the other hand in an outlet directed towards the outlet end of the spout. But these devices are not intended for oral inhalation of drugs for the treatment of lung or pulmonary diseases but simply consist in spray applicator devices for local treatment of conditions of the nose, mouth or throat. In fact their shape, wherein the angle between the longitudinal axis of the orifice (aerosol outlet) and the longitudinal axis of the valve stem of the canister is lower than 90°, makes these devices unsuitable for the administration to the lungs of a product by oral inhalation. Moreover the spout shape does clearly not resemble an inhaler mouthpiece.

In view of the above, there is a continued need for such actuators and metered-dose inhalers which allow a substantial fraction of non-respirable particles or droplets to be removed from an aerosol cloud before the aerosol cloud is dispensed through a mouthpiece opening without affecting other parameters of the emitted aerosol, such as the particle size distribution (PSD) and the respirable dose, and without increasing the size or significantly altering the shape of the inhaler.

SUMMARY OF THE INVENTION

Accordingly, it is one object of the present invention to provide novel actuators and metered-dose inhalers.

It is another object of the present invention to provide novel actuators and metered-dose inhalers which allow a substantial fraction of non-respirable particles or droplets to be removed from an aerosol cloud before the aerosol cloud is dispensed through a mouthpiece opening without affecting other parameters of the emitted aerosol, such as the particle size distribution (PSD) and the respirable dose, and without increasing the size or significantly altering the shape of the inhaler These and other objects, which will become apparent during the following detailed description, have been achieved by the inventors' discovery of an actuator for an aerosol inhalation device comprising:

a housing adapted to receive an aerosol canister containing a pressurised medicament formulation, provided with a metering valve having a hollow valve stem, a mouthpiece portion terminating in a mouthpiece opening through which the user inhales, wherein the longitudinal axis of the mouthpiece portion is located at an angle greater or equal to 90° to the direction of the longitudinal axis of the hollow valve stem;

a nozzle block defining a valve stem receptacle, an expansion chamber or sump, and an orifice to propel the aerosol formulation towards the mouthpiece opening characterized by the presence of a tubular element extending in the mouthpiece portion from the orifice aperture in a longitudinal axis substantially aligned with a longitudinal axis of the actuator mouthpiece portion and substantially coinciding with the orifice longitudinal axis.

In particular, said tubular element is positioned to enclose the orifice aperture within a recess.

Preferably, the tubular element is configured such that one of its terminal openings may be close fit to the nozzle block external surface, around the orifice aperture, so as to be in a continuous flow path with the orifice.

More preferably, the tubular element is configured such that one of its terminal openings is in a tight fit with the nozzle block external surface, around the orifice aperture, so as to be in a continuous flow path with the orifice.

In an alternative embodiment, the tubular element may be welded to the nozzle block external surface, around the orifice aperture.

In an alternative preferred embodiment, the tubular element may be formed on the lateral part of a shaped hollow cylindrical object suitable to be tightly fitted to the outside of the nozzle block, covering its lateral surfaces so as the tubular element is in a continuous flow path with the orifice.

In a further preferred alternative embodiment, the tubular element, the nozzle block, the housing for the aerosol canister and the mouthpiece portion form a single piece moulded actuator.

The tubular element has an internal diameter from 2 to 15 mm, preferably from 3 to 12 mm, even more preferably from 5 to 7 mm, and the particularly preferred diameter is equal to about 6 mm.

The tubular element has a length, i.e. the distance between its apertures, from 2 to 20 mm, preferably from 3 to 15 mm, even more preferably from 8 to 12 mm, and the particularly preferred lengths are equal to about 9, 10, and 11 mm.

The tubular element may also have a conventional thickness for this kind of devices known to the skilled in the art, however, suitable tubular element thickness may be from 0.1 to 3 mm or more, preferably from 0.2 to 2 mm, more preferably from 0.8 to 1.2 mm and most preferably of 1 mm.

The tubular element or the shaped hollow cylindrical object comprising in its lateral side a tubular element, suitable to be tightly fitted to the outside of the nozzle block, may be formed of the same material as the nozzle block or of a different material specifically suited to its purposes.

According to a further aspect of the present invention, there is provided a shaped hollow cylindrical object suitable to be tightly fitted to the outside of the nozzle block of an actuator for pMDI inhalers, covering its lateral surfaces and comprising in its lateral side a tubular element so as that the tubular element is in a continuous flow path with the nozzle block orifice.

According to another aspect of the present invention, there is provided an inhaler comprising the actuator of any one aspect or embodiment described herein, and a canister having a metering valve and containing a pressurised medicament formulation. The canister comprises a valve stem to be fitted into the valve stem receptacle formed in the nozzle block.

According to another aspect, there is provided a metered-dose inhaler actuator. The actuator comprises a housing having a mouthpiece portion and a canister receiving portion configured to receive a canister. The actuator further comprises a nozzle block disposed within the housing and defining a valve stem receptacle configured to receive a valve stem of the canister, an orifice in fluid communication with the valve stem receptacle to propel the aerosol formulation towards the mouthpiece opening and a tubular element extending in the mouthpiece portion from the orifice aperture in a longitudinal axis substantially aligned with a longitudinal axis of the actuator mouthpiece portion and substantially coinciding with the orifice longitudinal axis.

According to a further aspect of the present invention, there is provided a kit of parts comprising an actuator of an aerosol inhalation device, the shaped hollow cylindrical object suitable to be tightly fitted to the outside of the nozzle block and an aerosol canister containing a pressurised medicament formulation.

According to another aspect, a method is provided in which an actuator of any one aspect or embodiment described herein is used for dispensing an aerosol formulation from a canister. The method may be used to dispense the aerosol formulation without interaction with a human or animal body. The method may, for example, be used to dispense an aerosol formulation when priming a metered dose inhaler.

Another aspect of the present invention is the use of an actuator comprising a tube element according to any aspect or embodiment described herein for the reduction of the non-respirable dose and consequent potential oro-pharyngeal deposition of the dispensed aerosol formulation on actuation of the inhaler.

The presence of the tubular element according to the present invention manipulates the airflow internal to the mouthpiece portion of the actuator, creating an area of low velocity immediately after the orifice aperture and altering the expansion dynamics of the flashing liquid emitted by the orifice which results in significant advantages over the prior art.

Among the main advantages one is the significant reduction in the non-respirable, coarse fraction of the emitted aerosol medicament via inertial impaction and retention in the actuator than in the oro-pharynx. Non-respirable fraction is often associated with systemic side effects and oral candidiasis and dysphonia (in case of inhaled corticosteroid treatment).

In addition the presence of the tubular element has minimal, negligible impact on the particle size distribution (PSD) of the delivered particles having aerodynamic diameter lower than 9 µm. In fact, the PSD observed in vitro using Andersen Cascade Impactor (ACI) fitted with a USP throat (Apparatus 1, United States Pharmacopoeia—USP34-NF29) is extremely comparable with that of a conventional actuator.

An actuator according to the present invention, retaining the coarse dose on the tubular element wall via inertial impaction, may remove the requirement for add-on devices, spacers or holding chambers such as the Volumatic™ and AeroChamber Plus™, which prevent a large proportion of the coarse particles from the dose reaching the patient, but produce dramatically changes in the PSD with respect to "actuator only" products. This reduces the need to carry such add-on devices which are cumbersome and is an additional factor considering patient compliance.

The so called "cold Freon effect", in which high-velocity aerosol hits the back of the throat, causing hiccup and patients to stop inhaling prematurely, is minimized.

The patient generated airflow is identical to that generated in a conventional MDI actuator without the tubular element according to the present invention. Duration of plume and manner of patient use are also unaffected.

This kind of actuator is compatible with the pMDI aerosol formulation technology based on hydrofluoroalkane (HFA) propellants. The aerosol formulation may be an aerosol solution formulation or an aerosol suspension formulation. The aerosol formulation may contain at least one active ingredient in a propellant or in a propellant/solvent system and, optionally, further excipients. In particular with solution formulation comprising an alcohol co-solvent an optional low volatility component such as glycerol may be present.

The performance of this kind of actuator through-can-life is consistent.

Any eventual deposits of the medicament in the tubular element or in the mouthpiece portion of the actuator may be removed through conventional washing or cleaning techniques.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

The terms "active drug," "active ingredient," "active," "active compound", "active substance," and "therapeutic agent" are used synonymously.

The terms "nozzle block" or "nozzle assembly" are used synonymously to define an almost cylindrical element, which accommodates the valve stem of the aerosol canister and directs the emitted dose towards the mouthpiece. It rigidly extends in the actuator housing adapted to receive the canister from a central internal position of its base.

As used herein, the term "aligned" when referring to two axes means "coinciding or parallel to each other".

By "substantially aligned with" it is meant that the axes deviate by less 30 degrees, preferably less than 15 degrees, more preferably less than 5 degrees, even more preferably less than 3 degrees, even more preferably less than 2 degrees, even more preferably less than 1 degree.

By "substantially coinciding with" it is meant that the axes deviate by less 30 degrees, preferably less than 15 degrees, more preferably less than 5 degrees, even more preferably less than 3 degrees, even more preferably less than 2 degrees, even more preferably less than 1 degree, and that the axes are offset by no more than 10 mm, preferably no more than 5 mm, more preferably no more than 2 mm, even more preferably no more than 1 mm, even more preferably no more than 0.5 mm, even more preferably no more than 0.1 mm.

The term "longitudinal axis" refers to a center longitudinal axis of the respective concavity of component.

"Respirable fraction" also termed "fine particle fraction" refers to an index of the percentage of active particles which would reach the deep lungs in a patient.

The respirable fraction is calculated by the ratio between the "respirable dose" and the "delivered dose." They are evaluated in vitro using a Multistage Cascade Impactor such as an Andersen Cascade Impactor (Apparatus 1, United States Pharmacopoeia—USP34-NF29) fitted with a USP throat, also defined as induction port, according to procedures reported in common Pharmacopoeias.

The "delivered dose" is determined from the cumulative deposition in the apparatus, while the "respirable dose," also defined as "fine particle dose," is calculated from the deposition on Stages 3 (S3) to filter (AF) corresponding to particles ≤4.7 microns.

The "non-respirable" dose is the amount of larger aerosol particles which, upon inhalation, impact within the mouth and throat of the patient and may be swallowed, potentially causing side effects. It is determined by the amount of the emitted aerosol particles blocked at the level of the USP throat.

Exemplary embodiments of the present invention will now be described with reference to the drawings. The features of the embodiments may be combined with each other unless specifically stated otherwise.

Figure 2:
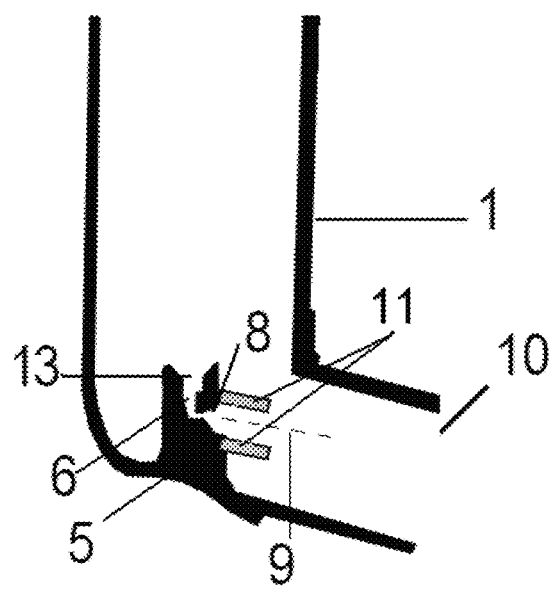
FIG. 2 is a schematic longitudinal sectional view of a pMDI actuator of an embodiment of the present invention.

FIG. 2 is a schematic cross-sectional view, taken along the center symmetry plane, of an actuator (1) for a pMDI inhaler according to the invention comprising a housing adapted to receive an aerosol canister containing a pressurised medicament formulation, provided with a metering valve and a hollow valve stem, a mouthpiece portion terminating in a mouthpiece opening 10 through which the user inhales, a nozzle block 5 defining a valve stem receptacle 13, an expansion chamber or sump 6, and an orifice 7 to propel the aerosol formulation towards the mouthpiece opening 10 characterised by the presence of a tubular element 11 extending in the mouthpiece portion from the orifice aperture 8 in a longitudinal axis 9 aligned with a longitudinal axis of the actuator mouthpiece portion and coinciding with the orifice 7 longitudinal axis, wherein said tubular element is positioned to enclose the orifice aperture 8 within a recess.

The tubular element 11 is configured such that one of its terminal openings may be close fit or in a tight fit to the with the nozzle block 5 external surface, around the orifice aperture 8, so as to be in a continuous flow path with said orifice.

One of the terminal openings of the tubular element 11 may be secured to the nozzle block external surface, around the orifice aperture to be in a continuous flow path with said orifice, using a suitable joining procedure such as welding, soldering or other suitable techniques such as by a chemical bonding process among which adhesive bonding. Adhesive bonding may be performed by depositing a suitable liquid adhesive or glue around the juncture circumference of one terminal opening of the tubular element and around the orifice aperture, optionally followed by curing the adhesive, e.g. with UV light.

Figures 3A, 3B, 3C:
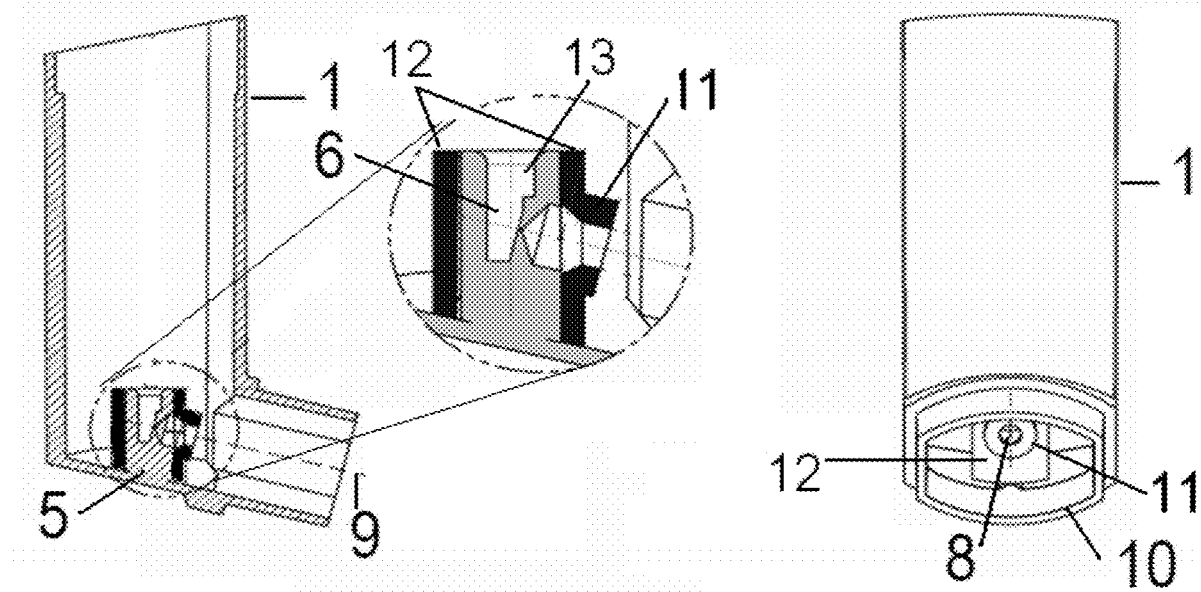
FIG. 3A is a schematic longitudinal sectional view of a pMDI actuator of another embodiment of the present invention, representing the hollow shaped hollow cylindrical object (in black), comprising in its lateral side a tubular element, suitable to be tightly fitted to the outside of the nozzle block.
FIG. 3B is an enlarged view of the actuator of FIG. 3A in the part comprising the hollow cylindrical object of FIG. 3A.
FIG. 3C is a front view of the pMDI actuator of FIG. 3A.

In an alternative preferred embodiment as shown in FIG. 3A to 3C the tubular element 11 may be formed on the lateral part of a shaped hollow cylindrical object 12 suitable to be tightly fitted to the outside of the nozzle block 5, covering its lateral surfaces, so as the tubular element 11 is in a continuous flow path with the orifice 7 and its aperture 8. In this case the hollow cylindrical object 12 and the tubular element 11 may be moulded in one piece, as a single unit, or, in alternative, they may be joined together around the lateral opening of the cylindrical object 12, at the level of the orifice aperture 8, and one of the terminal opening of the tubular element 11, using a suitable joining procedure such as welding, soldering or other suitable techniques such as by a chemical bonding process as described above.

In a further preferred alternative embodiment, the tubular element 11, the nozzle block 5, the housing for the aerosol canister and the mouthpiece portion of the actuator 1, according to the present invention, may be molded in one piece, as a single unit through single injection molding tools.

Figures 16A, 16B:
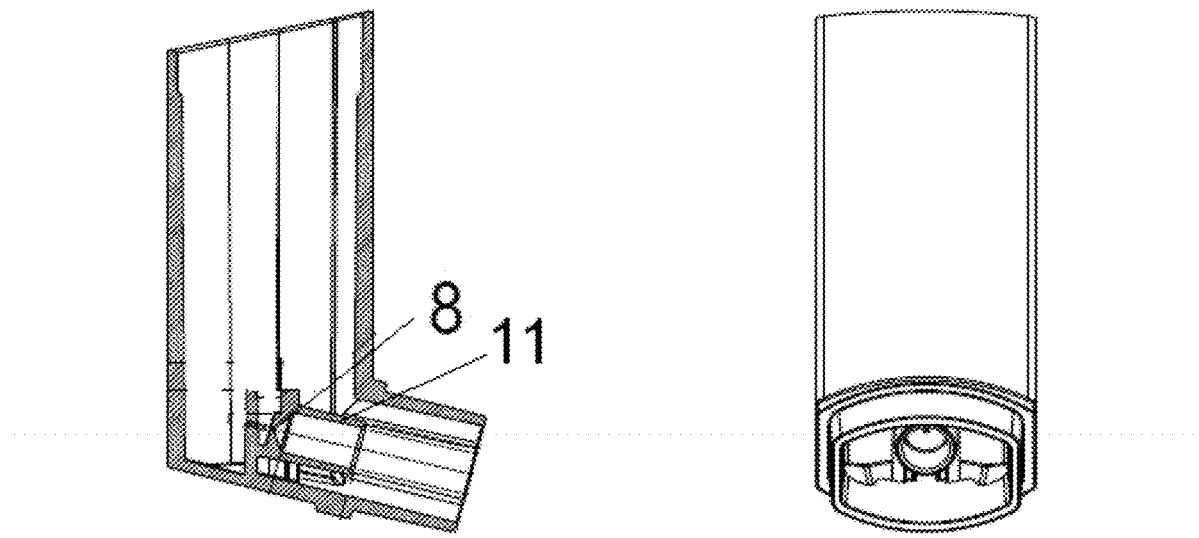
FIG. 16A is a schematic longitudinal sectional view of a pMDI actuator of an embodiment of the present invention, representing a single piece moulded actuator plus nozzle tube element with a smoothed gradient between the frusto-conical section of the orifice aperture and the tube opening.
FIG. 16B is a front view of the pMDI actuator of FIG. 16A.
Figures 17A, 17B, 17C:
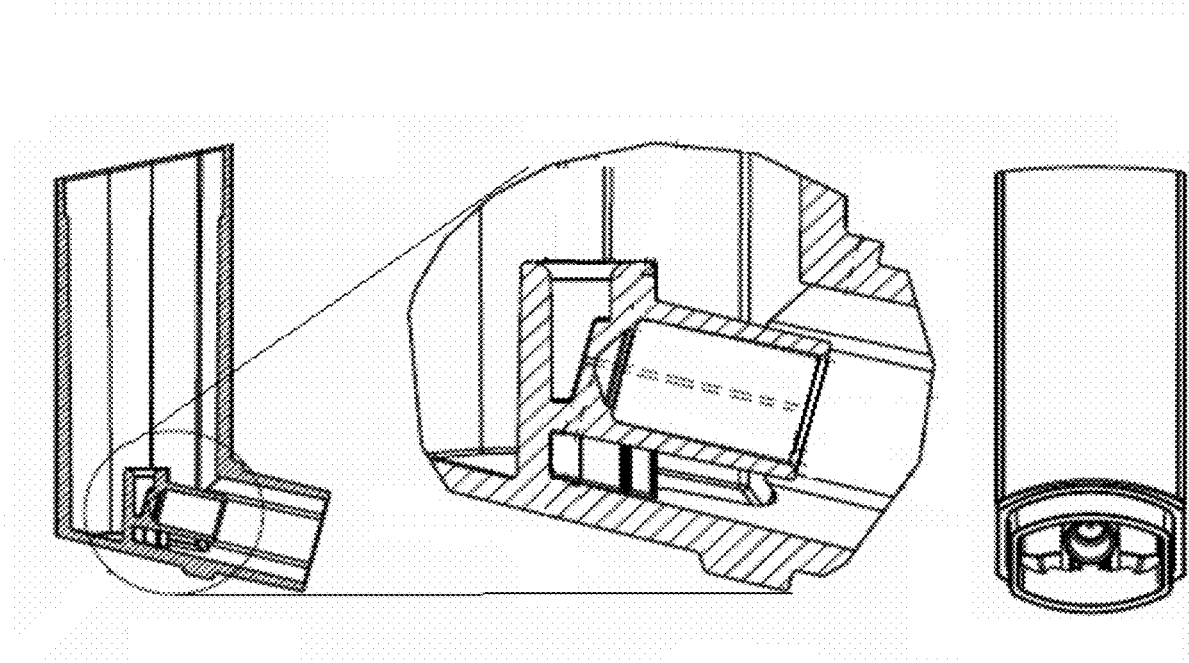
FIG. 17A is a schematic longitudinal sectional view of a pMDI actuator of an embodiment of the present invention, representing a single piece moulded actuator plus nozzle tube element with a stepped feature between the orifice aperture and the tube opening.
FIG. 17B is an enlarged view of the stepped actuator of FIG. 17A in the part of the tube element.
FIG. 17C is a front view of the stepped actuator of FIG. 17A.

The injection molding using the suitable tool permits manufacturing in a single piece an actuator plus nozzle tube element with a smoothed gradient between the frusto-conical section of the orifice aperture 8 and the tube opening, as shown in FIGS. 16A-16B, or with a stepped feature between the orifice aperture 8 and the tube opening, as shown in FIGS. 17A to 17C.

Actuation of the metering valve of the aerosol canister allows one dose of the formulation to be released from the valve through the stem 3, and propelled towards the mouthpiece opening passing respectively through the intermediate sump 6, orifice 7 and tubular element 11.

The tubular element 11 has a substantially cylindrical shape, opened at the two bases and with an internal diameter from 2 to 15 mm, preferably from 3 to 12 mm, even more preferably from 5 to 7 mm and a particularly preferred diameter is equal to about 6 mm.

The tubular element 11 has a length, i.e. the distance between its apertures, from 2 to 20 mm, preferably from 3 to 15 mm, even more preferably from 8 to 12 mm and particularly preferred lengths are equal to about 9, 10 and 11 mm.

Tubular elements with manufacturing tolerances of ±0.2 mm and preferably of ±0.1 mm with respect to a given diameter and/or length are acceptable and may be considered included in the present invention.

The tubular element 11 may also have a conventional thickness for this kind of devices known to the skilled in the art; however, suitable tubular element thickness may be from 0.1 to 3 mm or more, preferably from 0.2 to 2 mm, more preferably from 0.8 to 1.2 mm and most preferably 1 mm. In this case, manufacturing tolerances of from ±0.05 to ±0.2 are acceptable and are also included in the present invention.

Alternative embodiments of the present invention represented in FIG. 20(A) to (D) comprise tubular elements with a substantially cylindrical shape wherein non-parallel tubes as well as parallel tubes with an outer lip are provided and which may be categorized by the following geometric profiles:

Lipped Tubes (FIG. 20A): represented by parallel tubes consisting of various designs and features surrounding the exit orifice. The lipped tubes consisted of a range of parallel tubes (FIGS. 5-11) with either a lip of varied thickness (T), step length (S) and a smooth or a stepped feature around the exit orifice;

Narrow Divergent Tubes (FIG. 20B): represented by non-parallel tubes with a narrow entrance orifice ($d_1$=1.50±0.10 mm) which fits into the frusto-conical aperture of the actuator orifice 8;

Wide Divergent Tubes (FIG. 20C): represented by non-parallel tubes with a wide entrance orifice ($d_1$=4.50±0.10 mm) which fit externally, around the frusto-conical aperture of the actuator orifice 8; and Elliptical Tubes (FIG. 20D): represented by elliptical shaped tubes with various internal features such as oval or circular section or with internal partial obstructed airflow features.

The actuator 1, the nozzle block 5, the tubular element 11 and/or the shaped cylindrical object 12 may be formed of different materials and with different specifications which are suited for their specific purposes. Examples of suitable materials include metal materials such as aluminium, aluminium alloy or stainless steel; but also plastic polymeric materials, such as thermoplastic resins, optionally UV curable, including different grades of polypropylene (PP) the material of first choice in general for the pMDI actuators, polyethylene (i.e. HDPE, high density PE); fluorinated polymers such as polytetrafluoroethylene (PTFE); acrylonitrile-butadiene-styrene (ABS); polyacrylate such as polymethyl methacrylate (PMMA); polycarbonate (PC); polyamide (i.e. nylon); polyester such as polyethylene terephthalate (PET). Moreover the plastic polymeric materials may be coated with antistatic agents by means of a molding or a coating process.

The lateral surface of the tubular element 11 may be continuous or in alternative, perforated by one or more holes of optimised shapes (for instance round, square or rhomboid) and dimensions, disposed linearly or opposed each other and at different lengths and positions with respect to its opening in the mouthpiece portion of the actuator.

The lateral inner surface of the tubular element 11 may also present different alternative surface textures, in fact it may be smooth or wrinkled, with different degrees of roughness, to optimise the performance of the device.

The tubular element 11, the shaped hollow cylindrical object 12 suitable to be tightly fitted to the outside of the nozzle block and comprising in its lateral side a tubular element 11, or a single piece moulded actuator comprising the tubular element 11, the nozzle block 5, the housing for the aerosol canister 2 and the mouthpiece portion 9 are suitable for use in dispensing of a drug formulation to a patient through conventional pMDI inhalation devices.

The pMDI inhalation devices are known in the art. Said devices comprise a canister fitted with a metering valve.

Part or the entire canister may be made of a metal, for example aluminium, aluminium alloy, stainless steel or anodized aluminium. Alternatively the canister may be a plastic can or a plastic-coated glass bottle.

The metal canisters may have part or all of their internal surfaces lined with an inert organic coating. Examples of preferred coatings are epoxy-phenol resins, perfluorinated polymers such as perfluoroalkoxyalkane, perfluoroalkoxyalkylene, perfluoroalkylenes such as poly-tetrafluoroethylene (Teflon), fluorinated-ethylene-propylene (FEP), polyether sulfone (PES) or fluorinated-ethylene-propylene polyether sulfone (FEP-PES) mixtures or combination thereof. Other suitable coatings could be polyamide, polyimide, polyamideimide, polyphenylene sulfide or their combinations.

In certain embodiments canisters having their internal surface lined with FEP-PES or Teflon may be used.

In other particular embodiments canisters made of stainless steel may be used.

The canister is closed with a metering valve for delivering a daily therapeutically effective dose of the active ingredient. Generally the metering valve assembly comprises a ferrule having an aperture formed therein, a body molding attached to the ferrule which houses the metering chamber, a stem consisting of a core and a core extension, an inner- and an outer-seal around the metering chamber, a spring around the core, and a gasket to prevent leakage of propellant through the valve.

The gasket seal and the seals around the metering valve may comprise elastomeric material such as EPDM, chlorobutyl rubber, bromobutyl rubber, butyl rubber, or neoprene. EPDM rubbers are particularly preferred. The metering chamber, core and core extension are manufactured using suitable materials such as stainless steel, polyesters (e.g. polybutyleneterephthalate (PBT)), or acetals. The spring is manufactured from stainless steel eventually including titanium or other inert metal alloys. The ferrule may be made of a metal, for example aluminium, aluminium alloy, stainless steel or anodized aluminium. Suitable valves are available from manufacturers such as Valois, Bespak plc and 3M-Neotechnic Ltd.

The pMDI is actuated by a metering valve capable of delivering a volume of 25 to 100 μl, preferably 40 to 70 μl, and optionally about 50 μl, or about 63 μl per actuation.

In a typical arrangement the valve stem is seated in a nozzle block which has an orifice leading to an expansion chamber. The expansion chamber has an exit orifice 7 which extends into the mouthpiece. Actuator (exit) orifices having a diameter in the range 0.15-0.45 mm and a length from 0.30 to 1.7 mm are generally suitable. Preferably, an orifice having a diameter from 0.2 to 0.44 mm is used, e.g. 0.22, 0.25, 0.30, 0.33 or 0.42 mm.

In certain embodiments, it may be useful to utilize actuator orifices having a diameter ranging from 0.10 to 0.22 mm, in particular from 0.12 to 0.18 mm, such as those described in WO 03/053501, which is incorporated herein by reference in its entirety. The use of said fine orifices may also increase the duration of the cloud generation and, hence, may facilitate the coordination of the cloud generation with the slow inspiration of the patient.

The canister contains an aerosol formulation which may be an aerosol solution formulation or an aerosol suspension formulation. The aerosol formulation may contain at least one active ingredient in a propellant or in a propellant/solvent system and, optionally, further pharmaceutical acceptable additive or excipient.

The at least one active ingredient of the formulation may be any pharmaceutical active ingredient known in the art, administrable by inhalation alone or in combination for separate, sequential or simultaneous use. Preferably the active ingredient is known for prophylaxis or treatment of respiratory diseases and their symptoms, and in particular in diseases characterized by obstruction of the peripheral airways as a result of inflammation and presence of mucus, such as asthma of all types, chronic obstructive pulmonary disease (COPD), bronchiolitis, chronic bronchitis, emphysema, acute lung injury (ALI), cystic fibrosis, rhinitis, and adult or acute respiratory distress syndrome (ARDS).

The at least one active ingredient is selected from the class of the beta-2 agonists, inhaled corticosteroids, anti-muscarinic agents, phosphodiesterase IV inhibitors, and combinations thereof.

More preferably the beta-2 agonist is selected from the group of salbutamol, (R)-salbutamol (levalbuterol) fenoterol, formoterol, arformoterol, carmoterol (TA-2005), indacaterol, milveterol, vilanterol (GSK 642444), terbutaline, salmeterol, bitolterol, and metaproterenol in form of single stereoisomers, diastereoisomeric mixtures, and a pharmaceutically acceptable salt thereof or hydrate thereof.

More preferably the inhaled corticosteroid is selected from the group of beclometasone dipropionate, fluticasone propionate, fluticasone furoate, butixocort, mometasone furoate, triamcinolone acetonide, budesonide and its 22R-epimer, ciclesonide, flunisolide loteprednol, and rofleponide.

More preferably the anti-muscarinic agent is selected from the group of methscopolamine, ipratropium, oxitropium, tiotropium, glycopyrronium, aclidinium, umeclidinium, trospium and a salt thereof with a pharmaceutical acceptable counter ion. More preferably phosphodiesterase IV inhibitor is selected from the group of cilomilast, piclomilast, roflumilast, tetomilast, CHF 6001 and a pharmaceutically acceptable salt thereof.

Even more preferred active ingredients may be selected from the group of beclometasone dipropionate, fluticasone propionate, fluticasone furoate, mometasone furoate and budesonide alone or in combination with one or more active ingredient selected from salbutamol, formoterol, salmeterol, indacaterol, vilanterol, glycopyrronium, tiotropium, aclidinium, umeclidinium and a salt thereof.

The most preferred active ingredients are selected from beclometasone dipropionate, budesonide, formoterol fumarate, beclometasone dipropionate—salbutamol sulphate combination, beclometasone dipropionate—formoterol fumarate combination and beclometasone dipropionate—formoterol fumarate—glycopyrronium bromide combination.

The propellant may be any pressure-liquefied propellant and is preferably a hydrofluoroalkane (HFA) or a mixture of different HFAs, more preferably selected from the group consisting of HFA 134a (1,1,1,2-tetrafluoroethane), HFA 227 (1,1,1,2,3,3,3-heptafluoropropane), and mixtures thereof.

The solvent which may be incorporated into the formulation has generally a higher polarity than that of the propellant and may include one or more substances such as a pharmaceutically acceptable alcohol, in particular ethanol, a polyol, such as propylene glycol or polyethylene glycol, or mixtures thereof.

Advantageously the solvent is selected from the group of lower branched or linear alkyl ($C_1$-$C_4$) alcohols such as ethanol and isopropyl alcohol. Preferably the co-solvent is ethanol.

It is preferred that the at least one pharmaceutically active ingredient of the formulation is substantially completely and homogeneously dissolved in the propellant/solvent, system, i.e. the composition is preferably a solution formulation.

Optionally the formulation may comprise other pharmaceutical acceptable additives or excipients known in the art which are substantially inert materials which are non-toxic and do not interact in negative manner with other components of the formulation. In particular, the formulation may comprise one or more co-solvents, surfactants, carbohydrate, phospholipid, polymer, wetting agent, stabilizers, lubricants, or low volatility components.

Among the stabilizers, it is envisaged to use a suitable amount of an acid which may be organic or inorganic acid (mineral acids) which may be selected from pharmaceutically acceptable monoprotic or polyprotic acid, such as (but not limited to): hydrogen halides (hydrochloric acid, hydrobromic acid, hydroiodic acid, etc.) phosphoric acid, nitric acid, sulphuric acid, and halogen oxoacids.

Low volatility components are useful in order to increase the mass median aerodynamic diameter (MMAD) of the aerosol particles upon actuation of the inhaler and/or to improve the solubility of the active ingredient in the propellant/solvent system.

The low volatility component, when present, has a vapor pressure at 25° C. lower than 0.1 kPa, preferably lower than 0.05 kPa. Examples of low-volatility components are esters such as isopropyl myristate, ascorbyl myristate, tocopherol esters; glycols such as propylene glycol, polyethylene glycol, glycerol; and surface active agents such as saturated organic carboxylic acids (e.g. lauric, myristic, stearic acid) and unsaturated carboxylic acids (e.g. oleic or ascorbic acid).

The amount of low volatility component may vary from 0.1 to 10% w/w, preferably from 0.5 to 5% (w/w), more preferably from 1 and 2% (w/w).

In another embodiment, an amount of water comprised between 0.005 and 0.3% (w/w) may optionally be added to the formulations in order to favorably affect the solubility of the active ingredient without increasing the MMAD of the aerosol droplets upon actuation.

Other features of the invention will become apparent in the course of the following descriptions of exemplary embodiments which are given for illustration of the invention and are not intended to be limiting thereof.

EXAMPLES

Example 1A

Figure 4:
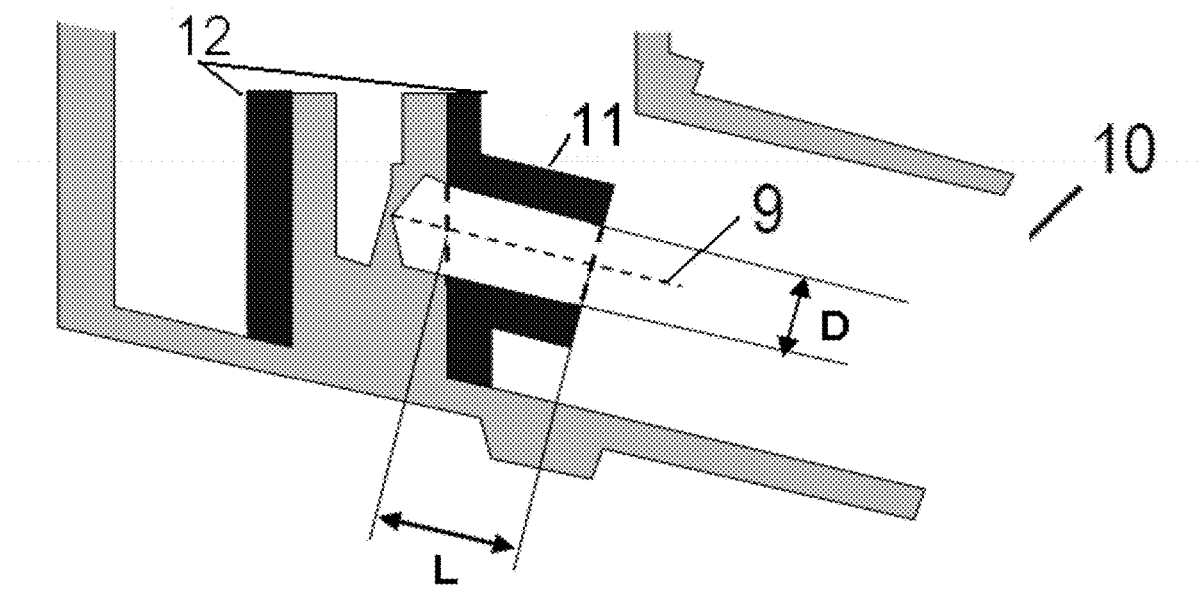
FIG. 4 is an enlarged sectional view of a portion of a pMDI actuator according to an embodiment wherein projections indicating the diameter (D) and the length (L) of the tubular element are shown.
Figure 5:
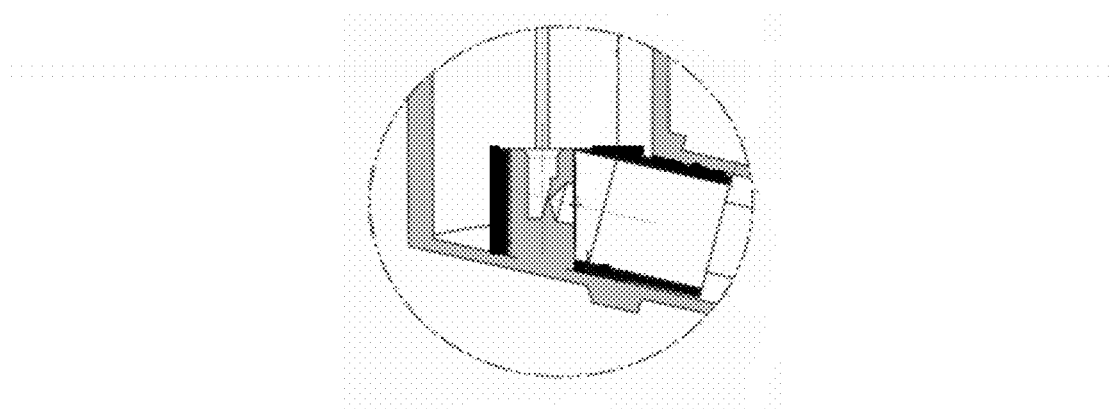
FIG. 5 is an enlarged sectional view of a portion of a pMDI actuator according to an embodiment wherein the internal diameter of the tube element was wider than the conical portion of the nozzle block of the actuator.

A range of tubular elements of predetermined dimensions were designed and manufactured. These were designed to allow them to be easily fitted to a conventional actuator block, thus converting the actuator into an actuator according to the present invention with a recessed orifice aperture design. FIGS. 3b and 4 show the basic premise of the design and the respective diameter D and length L of the geometries tested. The smallest internal diameter of 3 mm is less than the diameter of the orifice cone therefore was chamfered to prevent an impact surface and potential dead space from being created. The largest tube diameters required a step detail to enable the extra width to be catered for, as the internal diameter was wider than the nozzle block of the actuator (FIG. 5).

The tubular elements were manufactured in UV Curable Acrylic Plastic. All prototype tubes were fitted on actuators with 0.30 mm orifice diameter.

Figure 1:
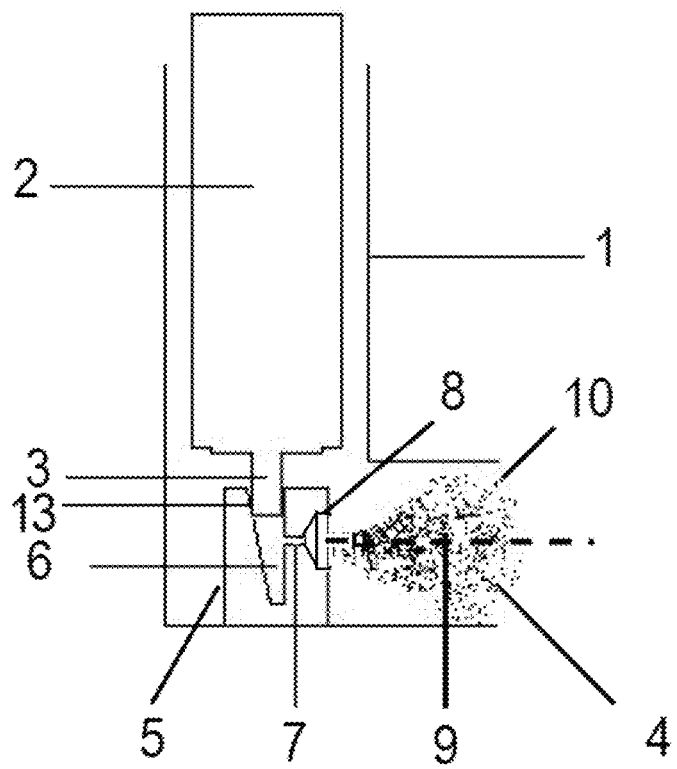
FIG. 1 is a schematic longitudinal sectional view of a conventional pressurized metered dose inhaler (pMDI) according to the prior art.

The actuator prototypes based on FIGS. 2 to 5 were produced and tested with respect to a conventional actuator of FIG. 1 with 0.30 mm orifice diameter.

All experiments used a solution formulation of beclometasone dipropionate 250 μg/dose (BDP 250) detailed in Table 1 and manufactured according to WO 98/56349A1, which is incorporated herein by reference in its entirety. The formulation was packaged in a standard aluminium 19 ml canister fitted with a conventional 50 μL valve.

TABLE 1

Target formulation for manufacture of BDP, 250 μg/50 μl.

| Component | Mass per Can (mg) | % w/w |
|---|---|---|
| BDP | 60.112 | 0.442 |
| Anhydrous Ethanol | 2040.000 | 15.000 |
| Glycerol | 176.800 | 1.300 |
| HFA 134a | 11323.088 | 83.258 |

Drug delivery characterization of the prototypes, in conjunction with the BDP 250 formulation, was determined with an Andersen Cascade Impactor (Apparatus 1, United States Pharmacopoeia—USP34-NF29) fitted with a USP throat, also defined as induction port, according to procedures reported in common Pharmacopoeias, at a flow rate of 28.3 (±5%) L min$^{-1}$. Drug deposition in each stage and in the induction port was quantified by UPLC/MS (Ultra-Performance Liquid Chromatography/Mass Spectrometry).

Aerosol characteristics determined include mass median aerodynamic diameter (MMAD), i.e., the diameter around which the mass aerodynamic diameters of the emitted particles are distributed equally; the delivered dose (DD) determined from the cumulative deposition in the apparatus, the fine particle dose (FPD) or respirable dose corresponding to the amount of particles of diameter ≤4.7 μm; the fine particle fraction (FPF) which is the percent ratio between the FPD and the DD. The range of tubular element geometries manufactured in phase 1 is reported in Table 2 and their drug delivery characteristics, analysed using the BDP 250 formulation of Table 1.

These results led to a production of a preferred narrower range of geometries for phase 2, surrounding the critical dimensions of 10 mm length for 6 mm diameter, for which phase 1 result had identified the performance to be most advantageous (Table 3). Note: two prototypes measuring a length (L) of 10 mm and internal diameter (D) of 6 mm were manufactured: prototype 189 (Table 2) and prototype 204 (Table 3).

TABLE 2

Phase 1: Prototype numbers for the geometries of tubular elements (prototypes 184-194).

| | | Length, L (mm) | | | |
|---|---|---|---|---|---|
| Prototypes | | 3 | 5 | 10 | 15 |
| Internal Diameter, D | 3 | 184 | 186 | 188 | 191 |
| | 6 | 185 | 187 | 189 | 192 |
| | 9 | | | 190 | 193 |
| | 12 | | | | 194 |

TABLE 3

Phase 2: Prototype numbers for the geometries of tubular elements (prototypes 197-211).

| | | Length, L (mm) | | | | |
|---|---|---|---|---|---|---|
| Prototypes | | 8 | 9 | 10 | 11 | 12 |
| Internal Diameter, D | 5 | 197 | 200 | 203 | 206 | 209 |
| | 6 | 198 | 201 | 204 | 207 | 210 |
| | 7 | 199 | 202 | 205 | 208 | 211 |

Figure 6:
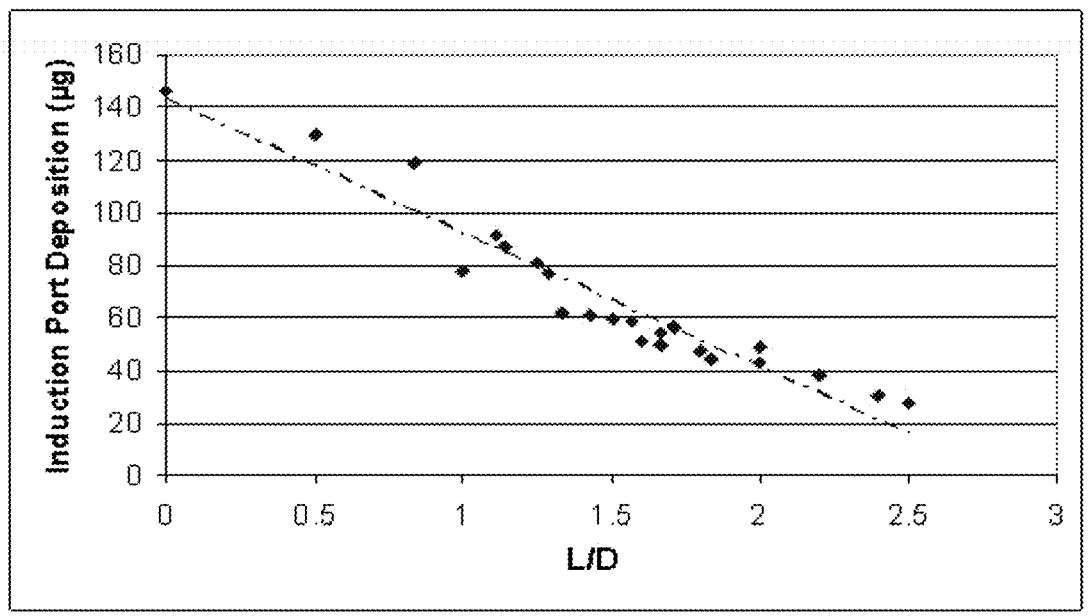
FIGS. 6 to 15 and FIGS. 18 to 19 represent graphics or images of the results of the tests performed in the Examples.
Figure 7:
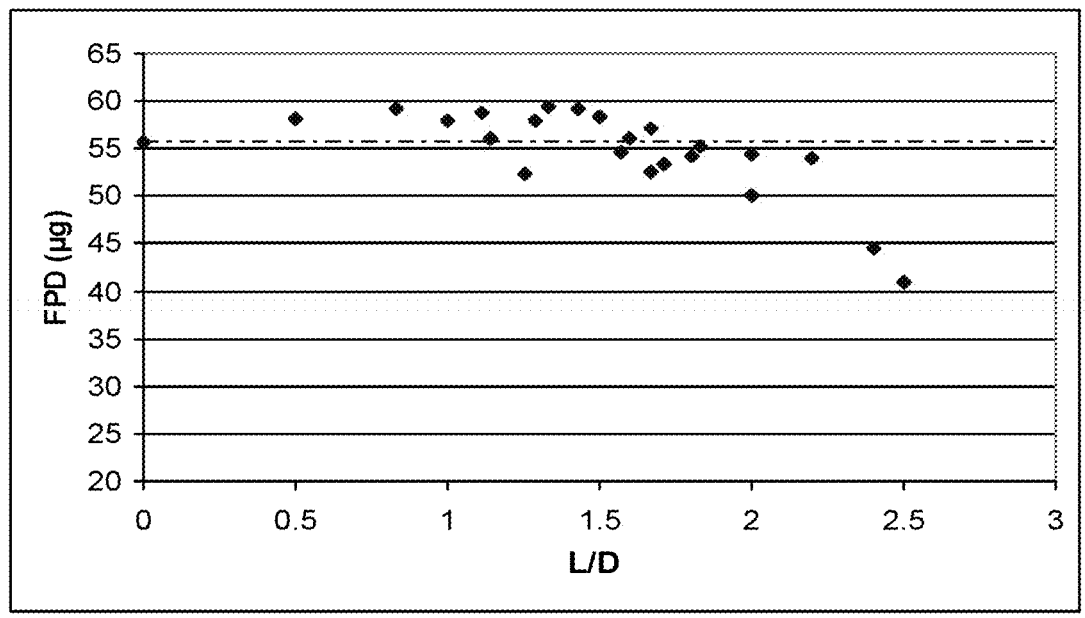

FIGS. 6 and 7 present data from both phases 1 and 2 and demonstrate correlations between the length/diameter ratio (L/D) of the tubular element, the induction port deposition and FPD respectively.

Increasing the L/D ratio of the tubular element results in a decrease in induction port deposition.

This may be a reflection of the relationship between the impacted mass and the emitted plume's cone angle. As the length of the tubular element increases, relative to the internal diameter, more of the particles from the plume may impact on the sides of the nozzle tube as the natural cone angle becomes increasingly restricted.

However, FIG. 7 shows that as the ratio is increased to greater than 2, the FPD begins to drop significantly, shifting the particle size distribution of the emitted aerosol particles away from that of the BDP 250 formulation emitted from a conventional actuator. This may be because the cone angle of the plume is restricted to such a degree that an increased number of the finer particles are impacted and retained on the tubular element in addition to the coarse fraction.

Therefore target drug delivery performance can be obtained by appropriate tubular element geometry selection.

Table 4 below presents combined data sets of phases 1 and 2, which best match the particle size distribution of the tested formulation (BDP 250: Table 1). All of these tube geometries reduce induction port deposition by a similar mass with respect to the same formulation delivered through a conventional actuator while maintaining constant the performance in term of Fine particle dose, MMAD and GSD (Geometric Standard Deviation). Similar reduction in induction port deposition from the selected prototypes suggests that potential slight differences in the final prototype geometry, caused by tolerances in the materials used in manufacture, will not affect the performance of the device.

TABLE 4

Data for a selection of the actuator prototypes with the tubular element, in comparison with a conventional actuator (n = number of canisters).

| Prototypes | Actuator fitted with tube element of different length L and internal diameter D (mm) | | | | | Conventional Actuator |
|---|---|---|---|---|---|---|
| | 197<br>L = 8,<br>D = 5<br>L/D = 1.6 | 204<br>L = 10,<br>D = 6<br>L/D = 1.7 | 205<br>L = 10,<br>D = 7<br>L/D = 1.4 | 207<br>L = 11,<br>D = 6<br>L/D = 1.8 | 211<br>L = 12,<br>D = 7<br>L/D = 1.7 | |
| Metered Dose (µg) | 226 | 232 ± 7 | 238 | 232 | 242 | 248 |
| Delivered Dose (µg) | 124 | 121 ± 5 | 136 | 113 | 124 | 225 |
| Induction Port deposition (µg) | 51 | 49 | 61 | 43 | 57 | 147 |
| FPD (µg) | 56 | 57 ± 2 | 59 | 55 | 53 | 56 |
| FPF (%) | 45 | 47 ± 1 | 44 | 49 | 43 | 25 |
| MMAD (µm) | 3.3 | 3.1 ± 0.1 | 3.2 | 3.3 | 3.2 | 3.4 |
| GSD | 2.1 | 2.1 ± 0.1 | 2.2 | 2.1 | 2.2 | 2.5 |
| n | 2 | 3 | 2 | 2 | 2 | 2 |

Example 1B

A range of single molded actuators plus tubular elements of 10 mm length and 6 mm diameter with smoothed or stepped nozzle tube features as shown in FIGS. 16A-B and in FIGS. 17A-C were manufactured and tested in their performances. The seven variants produced, depending also from the orifice diameters and the material types: Polypropylene (PP: Ineos 100-GA3), polymethylmetacrylate (PMMA: Aultglas V825T), Polycarbonate (PC: Makrolon 2405, are shown in Table 5

TABLE 5

Single moulded actuators plus tubular elements manufactured according to Example 1B.

| Prototype N. | Stepped Feature | Material | Orifice Diameter (mm) |
|---|---|---|---|
| 269 | Yes | Polypropylene | 0.32 |
| 270 | Yes | Polypropylene | 0.30 |
| 271 | No | Polycarbonate | 0.30 |
| 272 | No | Polycarbonate | 0.32 |
| 273 | Yes | Polycarbonate | 0.30 |
| 274 | Yes | Polycarbonate | 0.32 |
| 275 | No | Polymethylmetacrylate | 0.32 |

Example 2

An actuator fitted with one of the preferred tube element (i.e. Prototype 204 of Example 1A) with a 10 mm length (L) and 6 mm internal diameter (D) was tested to challenge the robustness of the concept. Through-can-life testing was carried out to assess the drug delivery performance of the prototype, in particular when no patient washing is performed, i.e. a "worst case" scenario. The plume temperature profile was also measured, to determine whether the presence of the nozzle tube could potentially reduce the "cold-freon" effect.

Through-Life-Testing

Prototype 204 was coupled with a new, un-primed can containing the solution formulation of beclometasone dipropionate 250 iµg/dose (BDP 250 of Table 1). Four doses were delivered to a waste Dose Unit Sampling Apparatus (DUSA; Copley Instruments, UK) every five minutes and all shot weights recorded. The five minute period allowed the ethanol to evaporate and the area around the orifice and nozzle tube to dry; this could be expected to occur between doses in everyday patient use. After every twenty doses, a microscope photograph was taken of the orifice aperture and tubular element. Andersen Cascade Impactor (ACI) testing was carried out at beginning, middle and end of can-use-life. Following the exhaustion of the can, the device was washed to determine the ease with which the layer of deposit within the recessed nozzle could be removed.

Figure 8:
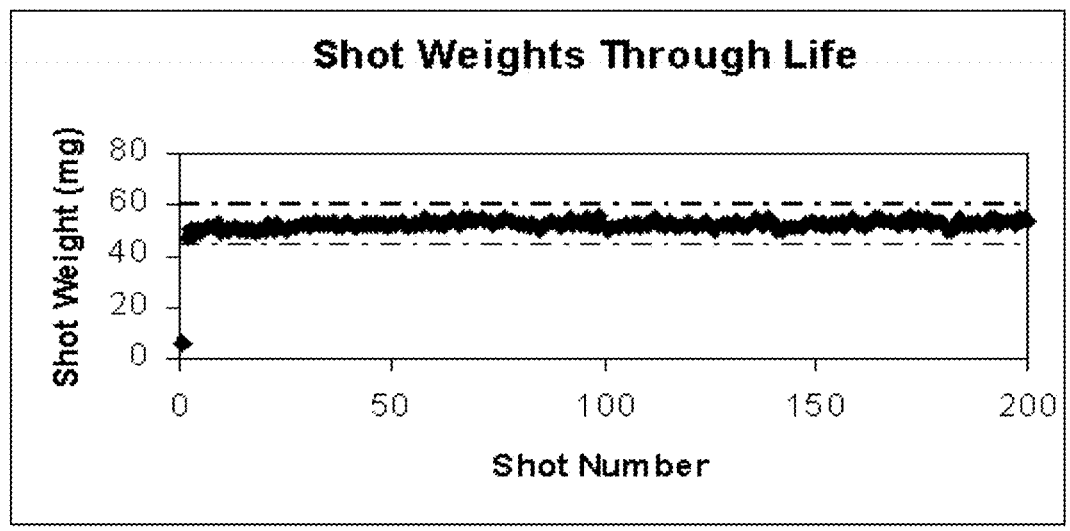

FIG. 8 presents the shot weight data for the through-can-life investigation. The mean shot weight was 52.6±1.3 mg, calculated from all shot weights (199) excluding the priming shot 1. All shot weights (excluding priming) are well within ±15% of the mean recorded shot weight.

The particle size distribution, as shown in Table 6 is consistent at beginning, middle and end of life of the canisters, suggesting that any deposit of drug and other non-volatile material on the internal surface of the tube element does not affect performance through-can-life.

TABLE 6

Data of Particle Size Distribution carried out at Beginning, Middle and End of Life for BDP 250 formulation coupled with the actuator having a tube element prototype 204.

| | Beginning of life | Middle of life | End of life |
|---|---|---|---|
| Metered Dose (µg) | 228 | NA | NA |
| Delivered Dose (µg) | 118 | 117 | 113 |
| FPD (µg) | 56 | 55 | 53 |
| FPF (%) | 48 | 47 | 47 |
| MMAD (µm) | 3.1 | 3.1 | 3.1 |
| n | 2 | 1 | 1 |

Figure 9:
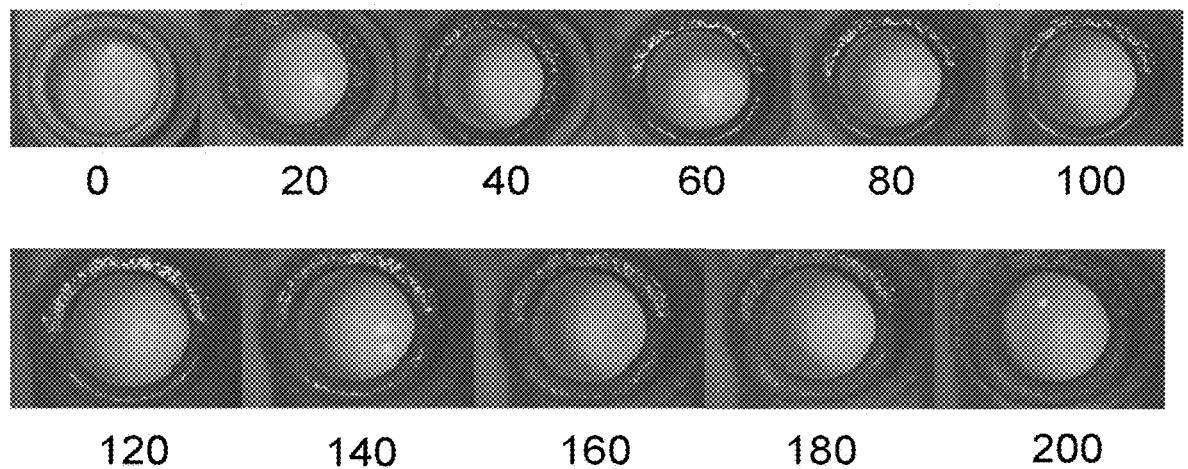

The microscope pictures of FIG. 9 show a gradual accumulation of non-volatile material, assumed to be mostly drug and glycerol particles, on the lower surface of the tubular element. This build up, however, does not block the orifice aperture and may be easily removed by washing the actuator with warm water, according to the washing procedures suggested for similar marketed products.

Plume Temperature

Plumes of the emitted aerosols were collected into a DUSA and temperature profiles were recorded by thermocouples (Omega, UK, K-Type, response time 3 ms) mounted 20 mm from the inlet of the DUSA. Data was collected continually by a PC using Dasylab Data Acquisition Software, to ensure that the entire plume temperature profile was captured, according to Brambilla,G.et al.,"Plume Temperature Emitted from Metered Dose Inhalers," *Int. J. Pharm.*, 405(1-2), 9-15, 2011, which is incorporated herein by reference in its entirety. Mean minimum plume temperature, (MMPT), for each test condition is reported as the mean±standard deviation of the lowest temperatures from each of five replicate plumes.

Figure 10:
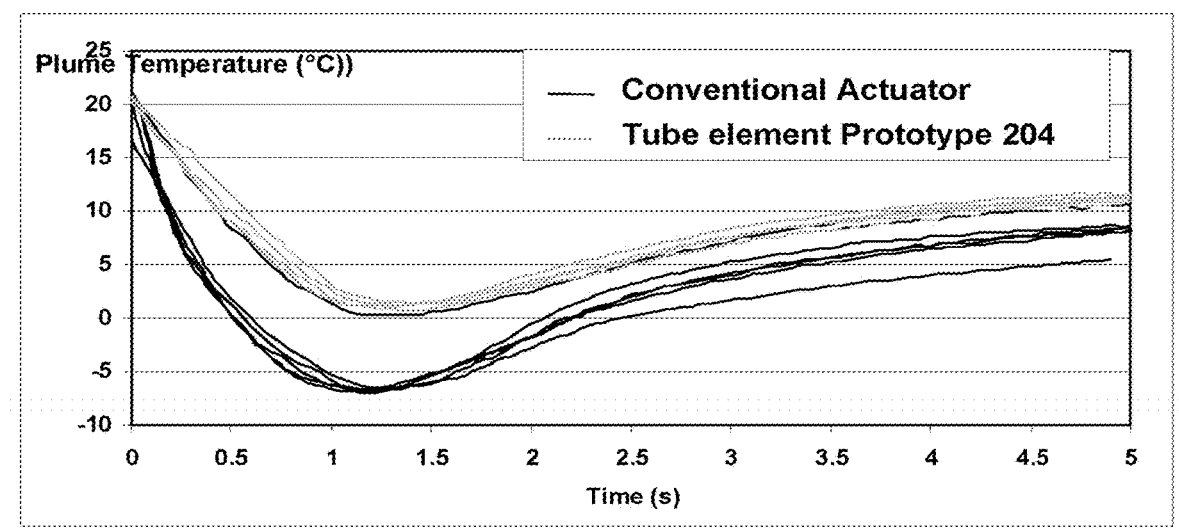
Figure 11:
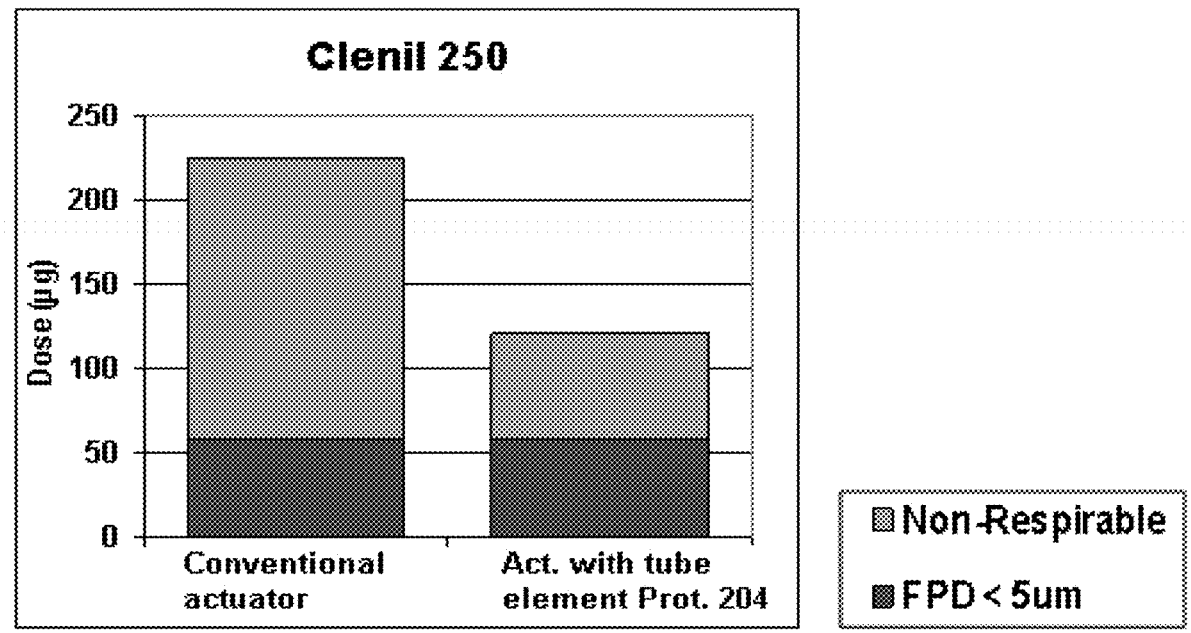
Figure 12:
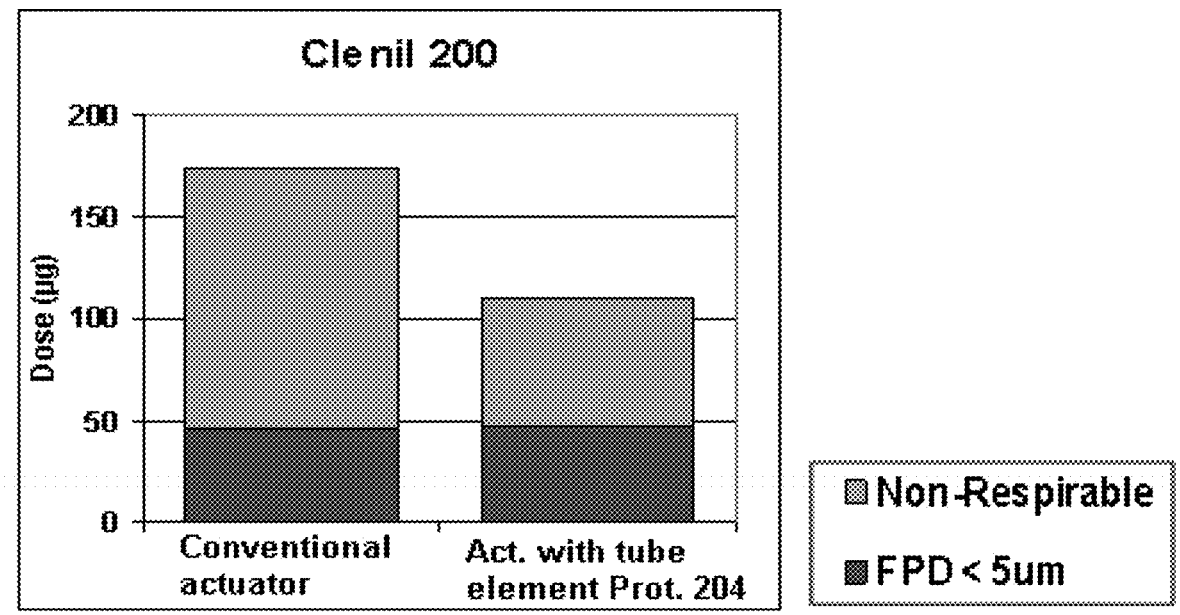
Figure 13:
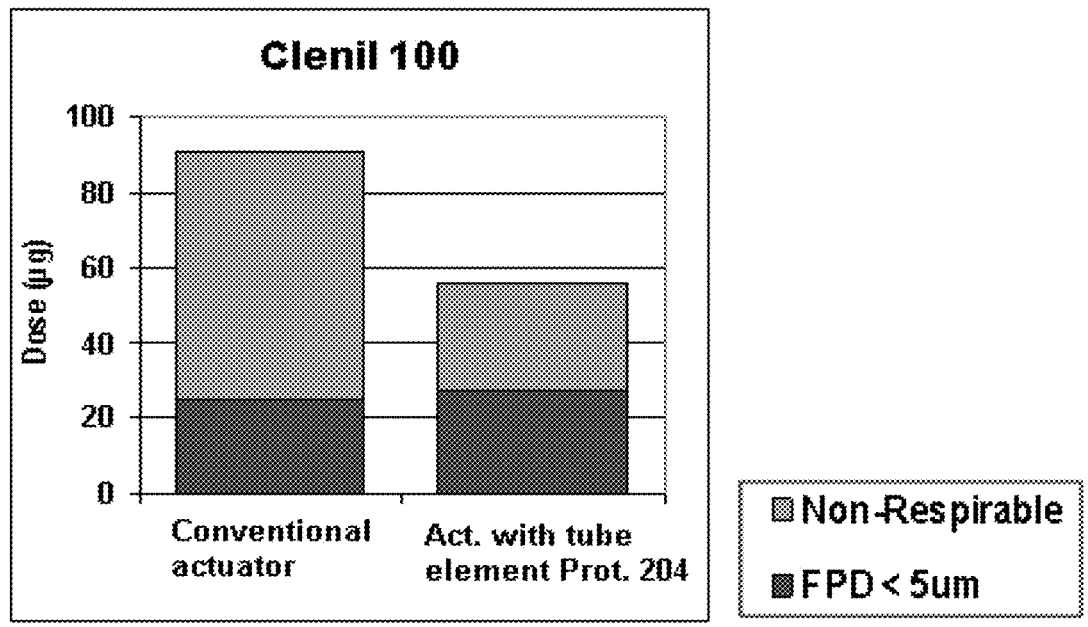
Figure 14:
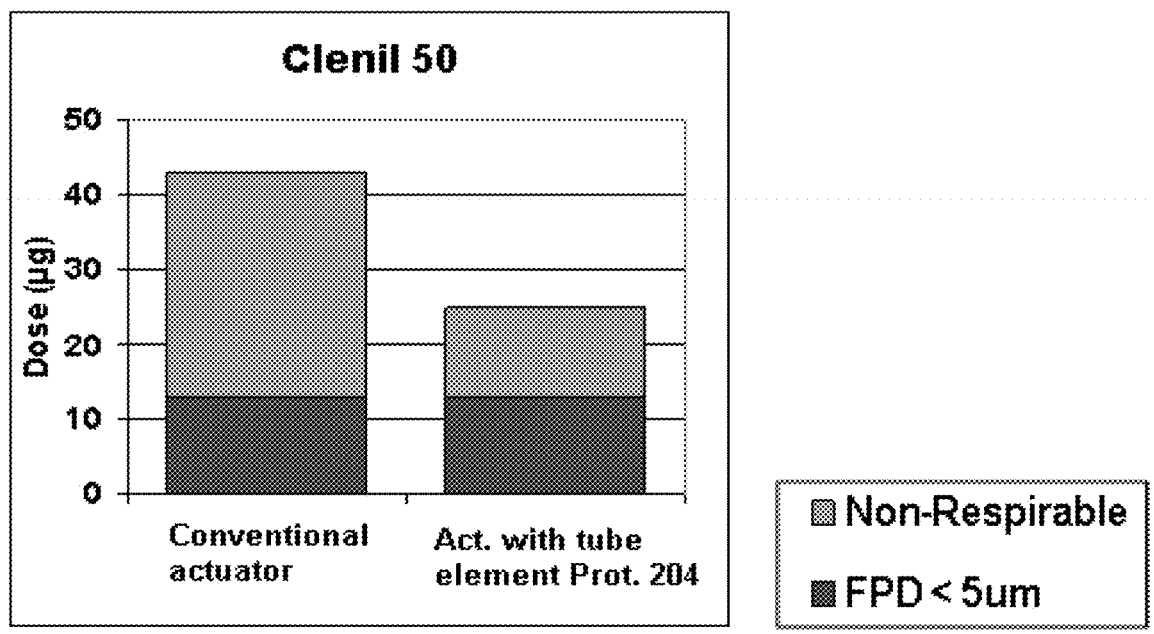

The presence of the recessed tube element causes an overall increase in the plume temperature profile, compared with a conventional actuator (0.30 mm orifice diameter) as shown in FIG. 10. The mean minimum plume temperature, MMPT, for the prototype is 0.9±0.4° C., compared with −5.9±1.9° C. without the nozzle tube. A warmer plume may cause less discomfort to the patient, which could have a more positive effect on patient compliance.

The presence of a tube element according to the invention also demonstrated a robust performance through-can-life, with consistent shot weight data and particle size distribution at beginning, middle and end of life of the canister. The plume temperature profile is also favourable when compared to a conventional pressurised metered dose inhaler actuator without tube element.

Example 3

Drug delivery investigations on the actuator according to the present invention, characterized by the presence of a tubular element, up to this point have used the BDP 250 solution formulation of Table 1, which mimics that of a commercialized formulation (Clenil Modulite 250). Four dose strengths of this product are currently marketed; therefore an actuators with tubular element prototype 204 was tested with each marketed formulation, to check whether the performance characteristics noted for BDP 250 (Clenil Modulite 250) noted so far are continued in analogous formulations with different dosage in active ingredient.

Drug delivery data was collected for the marketed Clenil Modulite range, purchased in a pharmacy, which includes the dose strengths: BDP 250, 200, 100, and 50 μg/50 μl. Data were also collected for Fostair, another marketed product, purchased in a pharmacy, based on a combination of the active ingredients beclometasone dipropionate and formoterol fumarate dihydrate 100 μg-6 μg, respectively per 50 μl actuation of a pressurised inhalation solution including ethanol, hydrochloric acid and norflurane (HFA 134a. The Fostair formulation does not contain glycerol.

Data was collected for each product as supplied, before the canister was removed and tested with an actuator provided with the tube element prototype 204 according to the invention. Data for all four strengths of the marketed Clenil Modulite are shown in FIGS. 11-14 and summarized in Table 7.

The particle size distributions for all products compare favourably with the results generated using prototype 204, while the induction port deposition is significantly reduced with the actuators with tube elements in place, therefore increasing the Fine Particle Fraction.

TABLE 7

Comparison of performance of Clenil with Conventional Actuator (as supplied) and Actuator with Tube Element prototype 204 (n = number of tested canisters).

| | Clenil Modulite 250 | | Clenil Modulite 200 | | Clenil Modulite 100 | | Clenil Modulite 50 | |
|---|---|---|---|---|---|---|---|---|
| | Conventional Actuator | Act. with Tube Elem Prototype 204 | Conventional Actuator | Act. with Tube Elem Prototype 204 | Conventional Actuator | Act. with Tube Elem Prototype 204 | Conventional Actuator | Act. with Tube Elem Prototype 204 |
| Metered Dose (μg) | 248 | 232 | 195 | 191 | 100 | 95 | 48 | 47 |
| Delivered Dose (μg) | 225 | 121 | 174 | 109 | 91 | 56 | 43 | 25 |
| Non-Respirable Dose (μg) | 168 | 64 | 128 | 62 | 66 | 28 | 30 | 12 |
| FPD (μg) | 57 | 57 | 46 | 47 | 25 | 27 | 13 | 13 |
| FPF (%) | 25 | 47 | 26 | 44 | 27 | 48 | 30 | 50 |
| MMAD (μm) | 3.4 | 3.1 | 3.4 | 3.4 | 3.3 | 3.3 | 3.2 | 2.9 |
| n | 2 | 3 | 2 | 2 | 2 | 2 | 2 | 2 |

Figure 15:
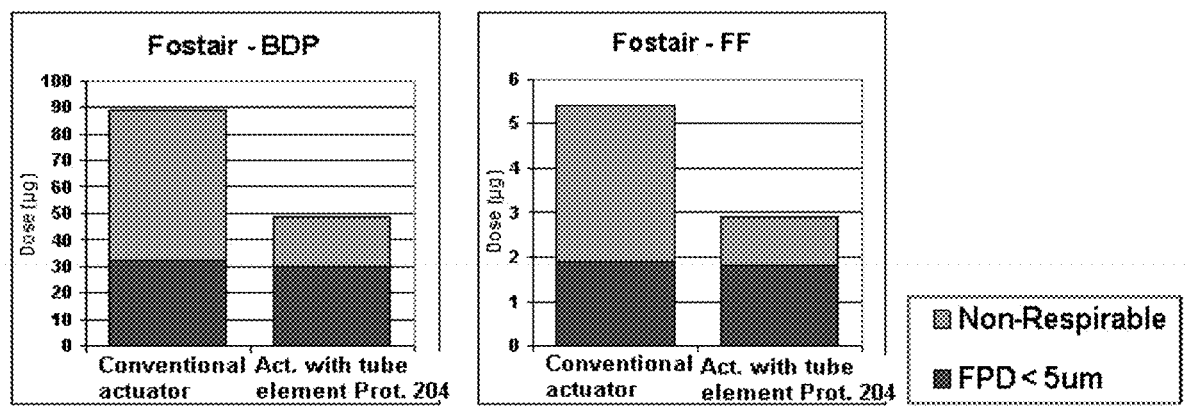

FIG. 15 and Table 8 demonstrate that an actuator with the tube element prototype 204 also functions effectively with the Fostair marketed formulation. The delivered dose is reduced from 89 to 49 μg and 5.4 to 2.9 μg for BDP and formoterol respectively, as induction port deposition is decreased.

TABLE 8

Comparison of performance of Fostair with Conventional Actuator (as supplied) and Actuator with Tube Element prototype 204 (n = number of tested canisters).

| | Fostair: BDP data | | Fostair: Formoterol data | |
|---|---|---|---|---|
| Actuator | Conventional | Act. with Tube Elem Prototype 204 | Conventional | Act. with Tube Elem Prototype 204 |
| Metered Dose (μg) | 98 | 93 | 6.0 | 5.5 |
| Delivered Dose (μg) | 89 | 49 | 5.4 | 2.9 |

TABLE 8-continued

Comparison of performance of Fostair with Conventional Actuator (as supplied) and Actuator with Tube Element prototype 204 (n = number of tested canisters).

| | Fostair: BDP data | | Fostair: Formoterol data | |
|---|---|---|---|---|
| Actuator | Conventional | Act. with Tube Elem Prototype 204 | Conventional | Act. with Tube Elem Prototype 204 |
| Non-Respirable Dose (µg) | 57 | 19 | 3.5 | 1.1 |
| FPD (µg) | 32 | 30 | 1.9 | 1.8 |
| FPF (%) | 36 | 61 | 35 | 63 |
| MMAD (µm) | 1.6 | 1.4 | 1.7 | 1.4 |
| n | 2 | 2 | 2 | 2 |

Having carried out all previous investigations using a formulation which mimics that of commercialized Clenil 250, the present results confirmed that an actuator provided with a tube element according to the present invention produced a similar effect in not only Clenil 200, 100 and 50, but also in Fostair, which is a combination of two active ingredients and does not contain a low volatility component such as glycerol.

The experiments performed showed that an actuator provided with a tube element according to the invention closely matched the Particle Size Distribution and Fine Particle Dose of the two commercial formulations, while significantly reducing the non-respirable dose and consequent potential oro-pharyngeal deposition.

Example 4

To ascertain if tube element material plays a role in either the retention and impaction of formulation or on the particle size distribution of the plume, tube elements of dimensions corresponding to prototype 204 (internal diameter: 6 mm; length: 10 mm) were manufactured in the following materials: aluminium, polytetrafluoro ethylene (PTFE), polypropylene (PP), stainless steel, nylon. They have been tested in an actuator with 0.32 orifice diameter using the BDP 250 formulation of Table 1 (Example 1A).

The results reported in Table 9 show that most materials demonstrated equivalent particle size distribution to BDP 250 with similar ability to reduce throat deposition. PTFE appeared to result in a lower FPD and higher throat deposition.

TABLE 9

Comparison of performance of BDP 250 formulation through actuators with tube elements in different materials and same dimensions as prototype 204 (mean of duplicate results).

| | PP | PTFE | Nylon | Aluminium | Stainless Steel |
|---|---|---|---|---|---|
| Metered Dose (µg) | 254 | 245 | 236 | 258 | 255 |
| Delivered Dose (µg) | 138 | 134 | 126 | 136 | 141 |
| Induction Port Deposition (µg) | 63 | 76 | 56 | 57 | 55 |
| FPD (µg) | 60 | 51 | 58 | 61 | 63 |
| FPF (%) | 44 | 38 | 46 | 45 | 45 |
| MMAD (µm) | 3.1 | 2.8 | 3.0 | 3.2 | 3.5 |
| GSD | 2.2 | 2.2 | 2.1 | 2.2 | 2.1 |
| Shot Wt (mg) | 55 | 54 | 55 | 55 | 56 |

Example 5

Drug delivery investigations on the actuator according to the present invention, characterized by the presence of a tubular element, were also performed with a pressurized metered dose inhaler containing a combination of two active ingredients wherein a first active ingredient is dissolved in the formulation and micronized particles of a second active ingredient are dispersed in the formulation.

Figure 18:
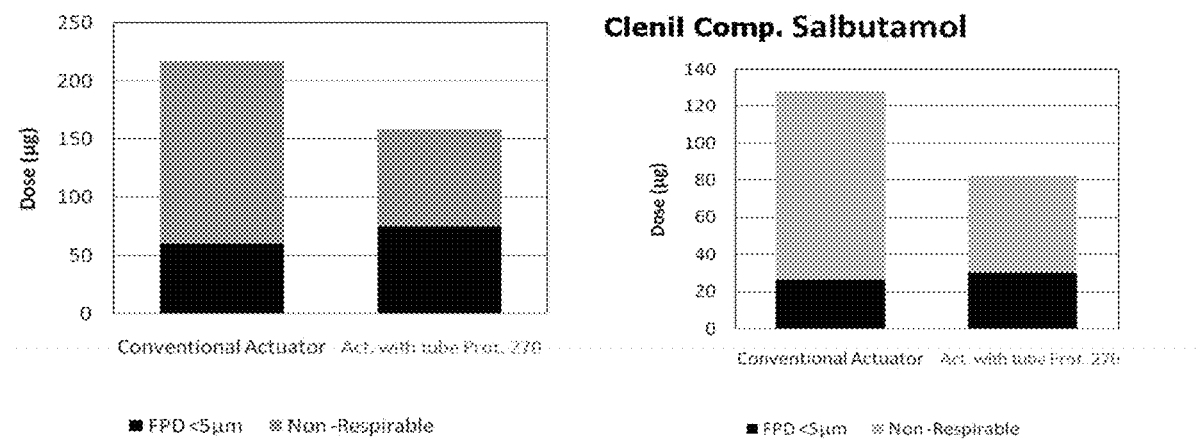

Data were collected for Clenil Compositum, a marketed product, purchased in a pharmacy, based on a combination of the active ingredients beclometasone dipropionate and salbutamol sulphate 250 µg-100 µg (as free salbutamol) respectively per 50 µl actuation of a pressurised inhalation formulation including ethanol, oleic acid and norflurane (HFA 134a) as inactive compounds. The data, collected for each product as supplied, before the canister was removed and tested with an actuator provided with the tube element prototype 270 according to the invention, are shown in FIG. 18 and summarised in Table 10.

Also in the case of a combination of one active ingredient in suspension and one active ingredient in solution the actuator according to the present invention results in an almost 50% reduction in the non-respirable dose both for beclometasone dipropionate and salbutamol. Pertinent choice of the orifice sizes allows aerosol plume to match more closely the fine particle dose of the conventional, marketed product.

These results are very important in reducing the potential exposure of both the active ingredients which may cause known important side effects such as, for the beta-2 agonist (salbutamol): tremor, headache and palpitation, while for the inhaled corticosteroid (beclometasone dipropionate) locally: oral candidiasis and dysphonia, and systemically: adrenal suppression, osteoporosis, decreased growth in children.

TABLE 10

Comparison of performance of Clenil Compositum formulation with Conventional Actuator (as supplied) and Actuator with Tube Element prototype 270 (n = number of tested canisters).

| | Clenil Compositum BDP data | | Clenil Compositum Salbutamol data | |
|---|---|---|---|---|
| Actuator | Conventional | Act. with Tube Elem Prototype 270 | Conventional | Act. with Tube Elem Prototype 270 |
| Delivered Dose (µg) | 216.9 | 158.5 | 128.6 | 82.4 |
| FPD (µg) | 60.2 | 74.6 | 26.7 | 30.5 |
| Non-Respirable Mass (µg) | 156.7 | 83.9 | 101.9 | 51.9 |
| N | 2 | 2 | 2 | 2 |

Example 6

Drug delivery investigations on the actuator according to the present invention, characterized by the presence of a tubular element, were also performed with a pressurized metered dose inhaler containing a triple combination of three different active ingredients dissolved in the formulation. In the experiment, a solution formulation of beclometasone dipropionate 100 µg/dose (BDP), formoterol fumarate 6 µg/dose (FF) and glycopyrronium bromide 12.5 µg/dose (GLY) detailed in Table 11 and manufactured according to WO 2011/076843A1 (which is incorporated herein by reference in its entirety), wherein anhydrous ethanol as cosolvent and 1M hydrochloric acid as stabilizing agent are added, was used. The formulation was packaged in a standard aluminium 19 ml canister fitted with a conventional 63 μL valve and a conventional actuator with 0.30 mm orifice diameter.

TABLE 11

Formulation of the triple combination of active ingredients of Example 6. (Content % w/w means the percent content by weight of each component with respect to the total weight of the formulation).

| Component | Mass per actuation (63 μL) | Content % (w/w) |
|---|---|---|
| BDP | 100 | 0.135 |
| FF | 6 | 0.0081 |
| GLY | 12.5 | 0.0169 |
| Ethanol | 8856 | 12.000 |
| 1M HCl | 14 | 0.0019 |
| HFA 134a | 64811.5 | 87.820 |

Figure 19:
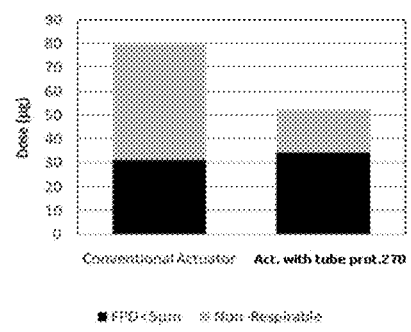
Figure 19:
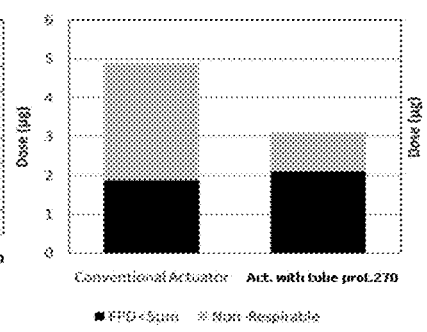
Figure 19:
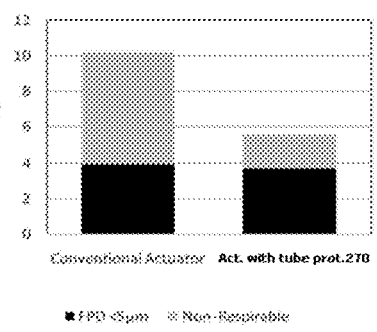
Figure 20:
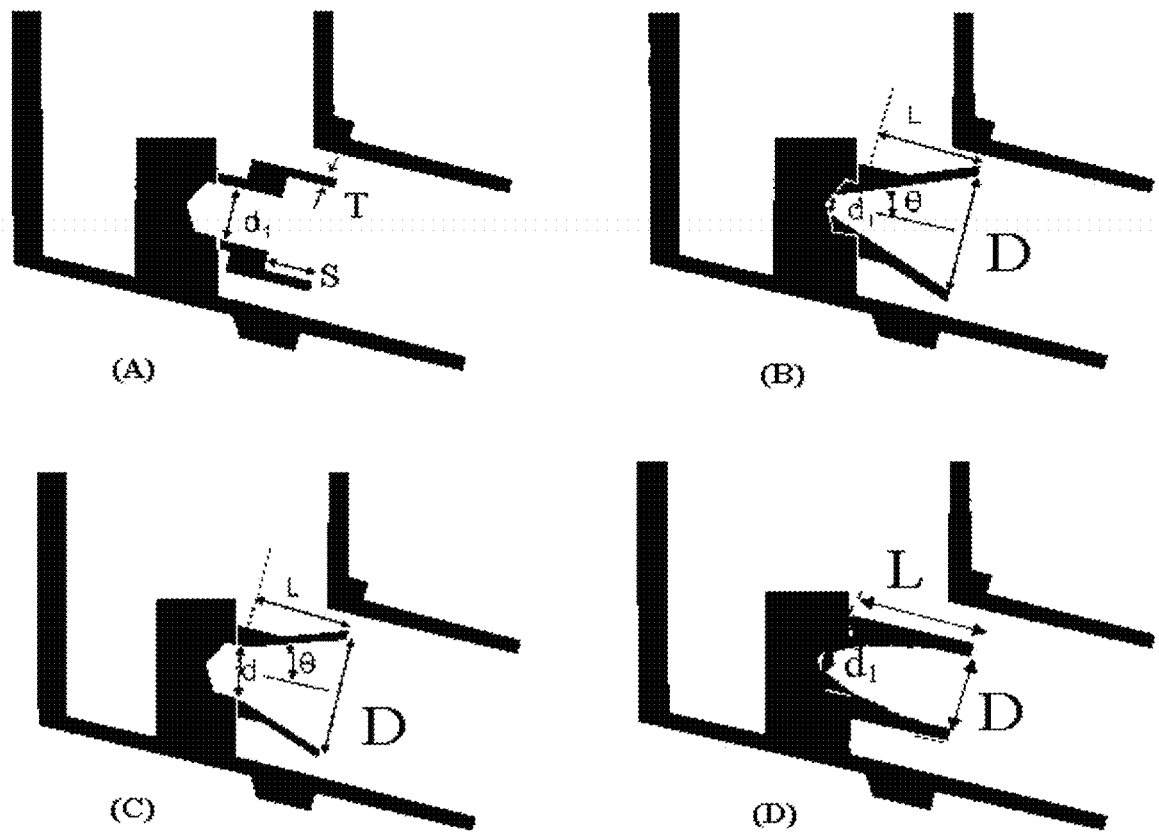
FIGS. 20(A), 20(B), 20(C), and 20(D) represent alternative embodiments of the tube element according to the present invention.

The data shown in FIG. 19 and summarized in Table 12 were collected for each of the active ingredients of the combination product, before the canister was removed and tested with an actuator having the same orifice diameter and length but provided with the tube element prototype 270 according to the present invention.

The experiment showed that the actuator provided with a tube element according to the invention closely matched the Fine Particle Dose of the combination delivered through a conventional actuator, while significantly reducing the non-respirable dose, of more than 30% and consequent potential oro-pharyngeal deposition.

TABLE 12

Comparison of performance of a triple formulation (BDP, FF, GLY) delivered with a conventional actuator and an actuator with tube element prototype 270 (n = number of tested canisters).

| | Triple combination BDP data | | Triple combination FF data | | Triple combination GLY data | |
|---|---|---|---|---|---|---|
| Actuator | Conventional | Act. with Tube Elem Prototype 270 | Conventional | Act. with Tube Elem Prototype 270 | Conventional | Act. with Tube Elem Prototype 270 |
| Delivered Dose (μg) | 79.8 | 52.6 | 4.9 | 3.1 | 10.2 | 5.6 |
| FPD (μg) | 31.5 | 34.3 | 1.9 | 2.1 | 3.9 | 3.7 |
| Non-Respirable Mass (μg) | 48.4 | 18.3 | 3.0 | 1.0 | 6.3 | 1.9 |
| n | 2 | 2 | 2 | 2 | 2 | 2 |

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An actuator for an oral aerosol inhalation device, comprising:

a housing adapted to receive an aerosol canister containing a pressurized medicament formulation, provided with a metering valve having a hollow valve stem with a longitudinal axis;

a mouthpiece portion terminating in a mouthpiece opening through which a user inhales;

a nozzle block defining a valve stem receptacle, an expansion chamber or sump, and an orifice, with an orifice aperture, to propel an aerosol formulation toward said mouthpiece opening; and a tubular element extending in the mouthpiece portion from the orifice aperture along a longitudinal axis aligned with a longitudinal axis of the mouthpiece portion and coinciding with a longitudinal axis of the orifice, wherein the longitudinal axis of the orifice in the nozzle block, aligned with the longitudinal axis of the mouthpiece portion, is arranged at an angle greater than or equal to 90° to a direction of the longitudinal axis of the hollow valve stem, and wherein the tubular element has an internal diameter in the range from 5 to 7 mm and a length in the range from 8 to 12 mm.

2. An actuator according to 1, wherein the tubular element is configured such that one of its terminal openings is close fit to an external surface of the nozzle block, around the orifice aperture, so as to be in a continuous flow path with the orifice and to enclose the orifice aperture within a recess.

3. An actuator according to claim 1, wherein the tubular element is secured to an external surface of the nozzle block, around the orifice aperture to be in a continuous flow path with the orifice.

4. An actuator according to claim 1, wherein the tubular element is on a lateral part of a shaped hollow cylindrical object tightly fitted to an outside of the nozzle block, covering its lateral surfaces such that the tubular element is in a continuous flow path with the orifice.

5. An actuator according to claim 1, wherein the tubular element, the nozzle block, the housing adapted to receive the aerosol canister, and the mouthpiece portion form a single piece moulded actuator.

6. An actuator according to claim 1, wherein at least one of the nozzle block, the tubular element, and a shaped hollow cylindrical object tightly fitted to an outside of the nozzle block, covering its lateral surfaces such that the tubular element is in a continuous flow path with the orifice, are formed of a same or different materials selected from metal materials selected from aluminium, aluminium alloy or stainless steel; plastic polymeric materials, selected from thermoplastic resins and UV curable, including different grades polypropylene or polyethylene; fluorinated polymers; an acrylate a polycarbonate; a polyamide; or a polyester.

7. An actuator according to claim 6, wherein the plastic polymeric material is coated with antistatic agents using a moulding or a coating process.

8. An oral inhaler comprising:
a canister having a metering valve and containing a pressurised medicament formulation; and
the actuator according to claim 1.

9. An oral metered-dose inhaler comprising:
a canister having a metering valve and containing a pressurised medicament formulation; and
the actuator according to claim 1.

10. An actuator according to claim 1, wherein a longitudinal axis of the orifice in the nozzle block, aligned with the longitudinal axis of the mouthpiece portion, is located at an angle in the range front greater than 90° to 120° to the direction of the longitudinal axis of the hollow valve stem.

11. An actuator according to claim 1, wherein the longitudinal axis of the orifice in the nozzle block, aligned with the longitudinal axis of the mouthpiece portion, is located at an angle in the range from greater than 90° to 110° to the direction of the longitudinal axis of the hollow valve stem.

12. An actuator according to claim 1, wherein a ratio of length to internal diameter of the tubular element is from 1.4 to 1.8, the ratio being set to remove an amount of non-respirable particles or droplets from a cloud of the aerosol formulation before the cloud of the aerosol formulation is dispensed through the mouthpiece opening.

13. An actuator according to claim 1, wherein a length of the tubular element is less than half a length of the mouthpiece portion.

14. An actuator according to claim 1, wherein the tubular element includes a hollow cylinder that extends along the longitudinal axis aligned with the longitudinal axis of the mouthpiece portion and coinciding with the longitudinal axis of the orifice.

15. A kit of parts comprising:
an aerosol canister containing a pressurised medicament formulation;
an actuator for an oral pMDI inhaler; and
a shaped hollow cylindrical component tightly fitted to an outside of a nozzle block of the actuator for the oral pMDI inhaler, covering lateral surfaces of the nozzle block, and comprising, in a lateral side, a tubular element arranged in a continuous flow path with an orifice, with an orifice aperture, of the nozzle block such that when the shaped hollow cylindrical object is tightly fitted to the outside of the nozzle block, said tubular element extends in a mouthpiece portion of the oral pMDI inhaler from the orifice aperture along a longitudinal axis aligned with a longitudinal axis of the mouthpiece portion and coinciding with a longitudinal axis of the orifice,
wherein the longitudinal axis of the orifice, aligned with the longitudinal axis of the mouthpiece portion, is at an angle greater than or equal to 90° to a direction of a longitudinal axis of a hollow valve stem of a canister seated in the nozzle block, and
wherein a ratio of length to internal diameter of the tubular element is from 1.4 to 1.8, the ratio being set to remove an amount of non-respirable particles or droplets from a cloud of an aerosol formulation before the cloud of the aerosol formulation is dispensed through the mouthpiece opening.

16. An actuator for an oral aerosol inhalation device, comprising:
a housing adapted to receive an aerosol canister containing a pressurized medicament formulation, provided with a metering valve having a hollow valve stem with a longitudinal axis;
a mouthpiece portion terminating in a mouthpiece opening through which a user inhales;
a nozzle block defining a valve stem receptacle, an expansion chamber or sump, and an orifice, with an orifice aperture, to propel an aerosol formulation toward said mouthpiece opening; and
a tubular element extending in the mouthpiece portion from the orifice aperture along a longitudinal axis aligned with a longitudinal axis of the mouthpiece portion and coinciding with a longitudinal axis of the orifice,
wherein the longitudinal axis of the orifice in the nozzle block, aligned with the longitudinal axis of the mouthpiece portion, is arranged at an angle greater than or equal to 90° to a direction of the longitudinal axis of the hollow valve stem, and
wherein a ratio of length to internal diameter of the tubular element is from 1.4 to 1.8, the ratio being set to remove an amount of non-respirable particles or droplets from a cloud of the aerosol formulation before the cloud of the aerosol formulation is dispensed through the mouthpiece opening.

17. An actuator according to claim 16, wherein the tubular element is on a lateral part of a shaped hollow cylindrical object tightly fitted to an outside of the nozzle block, covering its lateral surfaces such that the tubular element is in a continuous flow path with the orifice.

18. An actuator according to claim 16, wherein the tubular element, the nozzle block, the housing adapted to receive the aerosol canister, and the mouthpiece portion form a single piece moulded actuator.

19. An actuator according to claim 16,
wherein a length of the tubular element is less than half a length of the mouthpiece portion, and
wherein the tubular element includes a hollow cylinder that extends along the longitudinal axis aligned with the longitudinal axis of the mouthpiece portion and coinciding with the longitudinal axis of the orifice.

* * * * *